United States Patent
Bassett et al.

(10) Patent No.: US 8,506,296 B2
(45) Date of Patent: *Aug. 13, 2013

(54) DENTAL RESTORATIVE SYSTEM AND COMPONENTS

(75) Inventors: Jeffrey A. Bassett, Vista, CA (US); Kent Woolf, Oceanside, CA (US); Maurice Salama, Atlanta, GA (US); Henry Salama, Glenside, PA (US); David Garber, Atlanta, GA (US)

(73) Assignee: Zimmer Dental, Inc., Carlsbad, CA (US)

( * ) Notice: Subject to any disclaimer, the term of this patent is extended or adjusted under 35 U.S.C. 154(b) by 1026 days.

This patent is subject to a terminal disclaimer.

(21) Appl. No.: 11/380,560

(22) Filed: Apr. 27, 2006

(65) Prior Publication Data

US 2006/0286508 A1 Dec. 21, 2006

Related U.S. Application Data

(60) Provisional application No. 60/691,685, filed on Jun. 17, 2005, provisional application No. 60/714,641, filed on Sep. 7, 2005.

(51) Int. Cl.
*A61C 8/00* (2006.01)
(52) U.S. Cl.
USPC ......................................................... 433/173
(58) Field of Classification Search
USPC ......................................... 433/172–176, 167
See application file for complete search history.

(56) References Cited

U.S. PATENT DOCUMENTS

| 1,777,731 A | 10/1930 | Pavelka |
| 3,995,821 A | 12/1976 | Einhorn |
| 4,631,031 A | 12/1986 | Richter |
| 4,722,688 A | 2/1988 | Lonca |
| 4,738,623 A | 4/1988 | Driskell |
| 4,872,839 A | 10/1989 | Brajnovic |
| 4,897,007 A | 1/1990 | Chen et al. |
| 5,000,685 A | 3/1991 | Brajnovic |
| 5,035,619 A | 7/1991 | Daftary |
| 5,069,622 A | 12/1991 | Rangert et al. |

(Continued)

FOREIGN PATENT DOCUMENTS

| DE | 29706076 U1 | 9/1997 |
| EP | 0630621 A2 | 12/1994 |

(Continued)

OTHER PUBLICATIONS

International Search Report Dated Feb. 12, 2007.

(Continued)

*Primary Examiner* — Sunil K Singh
(74) *Attorney, Agent, or Firm* — Schwegman, Lundberg & Woessner P.A.

(57) ABSTRACT

Disclosed within is a dental restorative system including a dental abutment having a longitudinal axis, lingual and facial aspects, a base portion for engagement with a dental implant, and a tapered coronal portion. The dental abutment further includes an emergence profile portion between the base portion and the tapered coronal portion. The emergence profile portion includes at least a first concave surface and at least a first convex surface. The dental abutment may further include an interproximally sloping margin shoulder and a reduced terminal portion located at the upper end of the tapered coronal portion. Alternative embodiments of the dental abutment are also disclosed.

40 Claims, 23 Drawing Sheets

(56) References Cited

U.S. PATENT DOCUMENTS

| | | | |
|---|---|---|---|
| 5,073,111 A | 12/1991 | Daftary | |
| 5,087,200 A | 2/1992 | Brajnovic et al. | |
| 5,104,318 A | 4/1992 | Piche et al. | |
| 5,145,372 A | 9/1992 | Daftary et al. | |
| 5,297,963 A | 3/1994 | Dafatry | |
| 5,338,196 A | 8/1994 | Beaty et al. | |
| 5,362,235 A | 11/1994 | Daftary | |
| 5,417,570 A | 5/1995 | Zuest et al. | |
| 5,431,567 A | 7/1995 | Daftary | |
| 5,476,382 A | 12/1995 | Daftary | |
| D370,978 S | 6/1996 | Broberg et al. | |
| 5,547,377 A | 8/1996 | Daftary | |
| 5,591,029 A | 1/1997 | Zuest | |
| 5,642,996 A | 7/1997 | Mochida et al. | |
| 5,674,071 A | 10/1997 | Beaty et al. | |
| 5,688,123 A | 11/1997 | Meiers et al. | |
| D389,868 S | 1/1998 | Voorhees | |
| 5,755,574 A | 5/1998 | D'Alise | |
| 5,762,500 A * | 6/1998 | Lazarof | 433/213 |
| 5,779,480 A | 7/1998 | Groll et al. | |
| 5,810,592 A * | 9/1998 | Daftary | 433/173 |
| 5,816,813 A | 10/1998 | Hansson et al. | |
| 5,823,776 A | 10/1998 | Duerr et al. | |
| 5,829,981 A | 11/1998 | Ziegler | |
| 5,904,483 A | 5/1999 | Wade | |
| 5,915,968 A | 6/1999 | Kirsch et al. | |
| 5,938,444 A | 8/1999 | Hansson et al. | |
| D414,207 S | 9/1999 | Wagner et al. | |
| 5,989,029 A * | 11/1999 | Osorio et al. | 433/173 |
| 6,050,819 A * | 4/2000 | Robinson | 433/173 |
| 6,068,478 A | 5/2000 | Grande et al. | |
| 6,102,702 A | 8/2000 | Folsom et al. | |
| 6,129,548 A | 10/2000 | Lazzara et al. | |
| 6,132,060 A | 10/2000 | Gallo | |
| 6,142,782 A | 11/2000 | Lazarof | |
| 6,168,436 B1 | 1/2001 | O'Brien | |
| 6,174,167 B1 | 1/2001 | Wöhrle | |
| 6,217,333 B1 | 4/2001 | Ercoli | |
| 6,220,860 B1 | 4/2001 | Hansson | |
| 6,227,856 B1 * | 5/2001 | Beaty et al. | 433/172 |
| 6,280,195 B1 * | 8/2001 | Broberg et al. | 433/201.1 |
| 6,283,754 B1 | 9/2001 | Wöhrle | |
| 6,290,500 B1 | 9/2001 | Morgan et al. | |
| 6,332,777 B1 | 12/2001 | Sutter | |
| 6,358,052 B1 | 3/2002 | Lustig et al. | |
| D455,833 S | 4/2002 | Daftary | |
| 6,382,977 B1 | 5/2002 | Kumar | |
| 6,419,491 B1 | 7/2002 | Ricci et al. | |
| 6,454,569 B1 | 9/2002 | Hollander et al. | |
| D466,937 S | 12/2002 | Kochlefl et al. | |
| 6,488,501 B1 | 12/2002 | Harding | |
| 6,527,554 B2 | 3/2003 | Hurson et al. | |
| 6,540,514 B1 | 4/2003 | Falk et al. | |
| 6,540,516 B1 | 4/2003 | Ziegler | |
| 6,547,564 B1 | 4/2003 | Hansson | |
| 6,565,357 B1 | 5/2003 | Lazzara et al. | |
| D477,877 S * | 7/2003 | Whitehead | D24/156 |
| 6,619,958 B2 | 9/2003 | Beaty et al. | |
| 6,655,961 B2 | 12/2003 | Cottrell | |
| 6,663,389 B1 | 12/2003 | Gallicchio | |
| 6,672,872 B2 | 1/2004 | Cottrell | |
| 6,758,672 B2 | 7/2004 | Porter et al. | |
| 6,824,386 B2 | 11/2004 | Halldin et al. | |
| 6,840,770 B2 | 1/2005 | McDevitt | |
| 6,846,180 B1 | 1/2005 | Joos | |
| D503,432 S | 3/2005 | Huang | |
| 6,887,275 B2 | 5/2005 | Carchidi et al. | |
| D507,306 S | 7/2005 | Siegel | |
| D508,533 S | 8/2005 | Siegel | |
| 6,951,460 B2 | 10/2005 | Halldin et al. | |
| 6,981,873 B2 | 1/2006 | Choi et al. | |
| D523,145 S | 6/2006 | Gabrielsson | |
| 7,090,494 B2 | 8/2006 | Shelemay et al. | |
| 7,163,398 B2 | 1/2007 | Klardie et al. | |
| 7,179,088 B2 | 2/2007 | Schulter | |
| D582,041 S | 12/2008 | Bassett et al. | |
| 8,007,279 B2 | 8/2011 | Bassett et al. | |
| 2001/0034008 A1 | 10/2001 | Porter et al. | |
| 2002/0039718 A1 | 4/2002 | Kwan | |
| 2002/0098060 A1 | 7/2002 | Kochlefl et al. | |
| 2002/0127515 A1 | 9/2002 | Gittleman | |
| 2003/0068599 A1 | 4/2003 | Balfour et al. | |
| 2003/0082499 A1 | 5/2003 | Halldin et al. | |
| 2003/0124489 A1 | 7/2003 | Hurson et al. | |
| 2003/0148246 A1 | 8/2003 | Lustig et al. | |
| 2003/0175655 A1 | 9/2003 | Klardie et al. | |
| 2003/0190586 A1 | 10/2003 | Falk et al. | |
| 2003/0211445 A1 | 11/2003 | Klardie et al. | |
| 2004/0029075 A1 | 2/2004 | Peltier et al. | |
| 2004/0096804 A1 | 5/2004 | Vogt et al. | |
| 2004/0121286 A1 | 6/2004 | Aravena et al. | |
| 2004/0142304 A1 | 7/2004 | Cottrell | |
| 2004/0185417 A1 * | 9/2004 | Rassoli | 433/173 |
| 2004/0185419 A1 | 9/2004 | Schulter et al. | |
| 2004/0209227 A1 | 10/2004 | Porter et al. | |
| 2004/0219488 A1 | 11/2004 | Choi et al. | |
| 2004/0234926 A1 | 11/2004 | Halldin et al. | |
| 2004/0241610 A1 | 12/2004 | Hurson | |
| 2005/0100861 A1 | 5/2005 | Choi et al. | |
| 2005/0136378 A1 | 6/2005 | Ennajimi et al. | |
| 2006/0078847 A1 | 4/2006 | Kwan | |
| 2006/0121416 A1 | 6/2006 | Engman | |
| 2006/0199150 A1 * | 9/2006 | Niznick | 433/173 |
| 2006/0199152 A1 | 9/2006 | Hurson et al. | |
| 2006/0204928 A1 * | 9/2006 | Hurson | 433/173 |
| 2007/0037122 A1 | 2/2007 | Bassett et al. | |
| 2009/0176191 A1 | 7/2009 | Gahlert | |

FOREIGN PATENT DOCUMENTS

| | | |
|---|---|---|
| EP | 0879024 | 11/1998 |
| EP | 08790225 | 11/1998 |
| EP | 1118312 | 7/2001 |
| EP | 1462066 | 9/2004 |
| EP | 1898827 A2 | 3/2008 |
| FR | 2737847 A1 | 2/1997 |
| JP | 7299081 A | 11/1995 |
| JP | 10043207 A | 2/1998 |
| JP | 11503655 A | 3/1999 |
| JP | 2005507284 A | 3/2005 |
| WO | 97/37610 A1 | 10/1997 |
| WO | 9852490 | 11/1998 |
| WO | 0149199 | 7/2001 |
| WO | 03030768 | 4/2003 |
| WO | 03/037208 A1 | 5/2003 |
| WO | 03047455 | 6/2003 |
| WO | WO-03105710 A2 | 12/2003 |
| WO | 2004/103202 A1 | 12/2004 |
| WO | WO-2005044134 A1 | 5/2005 |
| WO | 2005/072639 A1 | 8/2005 |

OTHER PUBLICATIONS

International Search Report from PCT/US06/23128 Dated Sep. 24, 2007.

Extended European Search Report—the supplementary European Search Report and European Search Opinion to PCT/US2006023130 dated Nov. 3, 2009.

Extended European Search Report—the supplementary European Search Report and European Search Opinion to PCT/US2006023128 dated Dec. 4, 2009.

U.S. Appl. No. 11/380,569, filed Apr. 27, 2006, Dental Restorative System and Components.

"U.S. Appl. No. 11/380,569, Final Office Action mailed Jun. 17, 2010", 15 pgs.

"U.S. Appl. No. 11/380,569, Final Office Action mailed Sep. 26, 2011", 11 pgs.

"U.S. Appl. No. 11/380,569, Non Final Office Action mailed Jan. 20, 2011", 15 pgs.

"U.S. Appl. No. 11/380,569, Non Final Office Action mailed Apr. 26, 2012", 10 pgs.

"U.S. Appl. No. 11/380,569, Non Final Office Action mailed Dec. 18, 2009", 12 pgs.

"U.S. Appl. No. 11/380,569, Response filed Mar. 22, 2010 to Non Final Office Action mailed Dec. 18, 2009", 12 pgs.

"U.S. Appl. No. 11/380,569, Response filed Apr. 20, 2011 to Non Final Office Action mailed Jan. 20, 2011", 17 pgs.

"U.S. Appl. No. 11/380,569, Response filed May 18, 2009 to Restriction Requirement mailed Mar. 19, 2009", 2 pgs.

"U.S. Appl. No. 11/380,569, Response filed Sep. 13, 2010 to Final Office Action mailed Jun. 17, 2010", 19 pgs.

"U.S. Appl. No. 11/380,569, Response filed Sep. 16, 2009 to Restriction Requirement mailed Aug. 28, 2009", 2 pgs.

"U.S. Appl. No. 11/380,569, Response filed Dec. 23, 2011 to Final Office Action mailed Sep. 26, 2011", 20 pgs.

"U.S. Appl. No. 11/380,569, Restriction Requirement mailed Mar. 19, 2009", 5 pgs.

"U.S. Appl. No. 11/380,569, Restriction Requirement mailed Aug. 28, 2009", 7 pgs.

"U.S. Appl. No. 29/249,358, Notice of Allowance mailed Jul. 25, 2008", 10 pgs.

"U.S. Appl. No. 29/249,358, Preliminary Amendment filed Jan. 11, 2007", 3 pgs.

"European Application Serial No. 06773137.2, Office Action mailed May 9, 2012", 4 pgs.

"European Application Serial No. 06784866.3, Response filed Apr. 20, 2012 to Office Action mailed Dec. 12, 2011", 12 pgs.

"International Application Serial No. PCT/US2006/023128, International Preliminary Report on Patentability mailed Dec. 17, 2007", 6 pgs.

"International Application Serial No. PCT/US2006/023128, International Search Report mailed Sep. 24, 2007", 3 pgs.

"International Application Serial No. PCT/US2006/023128, Written Opinion mailed Sep. 24, 2007", 5 pgs.

"International Application Serial No. PCT/US2006/023129, International Preliminary Report on Patentability mailed Dec. 17, 2007", 6 pgs.

"International Application Serial No. PCT/US2006/023129, International Search Report mailed Dec. 19, 2006", 1 pg.

"International Application Serial No. PCT/US2006/023129, Written Opinion mailed Dec. 19, 2006", 5 pgs.

"International Application Serial No. PCT/US2006/023130, International Preliminary Report on Patentability mailed Dec. 17, 2007", 7 pgs.

"International Application Serial No. PCT/US2006/023130, International Search Report mailed Feb. 12, 2007", 1 pg.

"International Application Serial No. PCT/US2006/023130, Written Opinion mailed Feb. 12, 2007", 6 pgs.

"Japanese Application Serial No. 2008-517052, Office Action mailed May 8, 2012", (With English Translation), 6 pgs.

"U.S. Appl. No. 11/380,569, Examiner Interview Summary mailed Jul. 17, 2012", 3 pgs.

"U.S. Appl. No. 11/380,569, Notice of Allowance mailed Jan. 2, 2013", 7 pgs.

"U.S. Appl. No. 11/380,569, Notice of Allowance mailed Sep. 25, 2012", 7 pgs.

"U.S. Appl. No. 11/380,569, Supplemental Notice of Allowability mailed Mar. 12, 2013", 5 pgs.

"Canadian Application Serial No. 2,611,827, Office Action mailed Jan. 25, 2013", 2 pgs.

"Canadian Application Serial No. 2,611,929, Office Action mailed Dec. 27, 2012", 2 pgs.

"Canadian Application Serial No. 2,611,942, Office Action mailed Dec. 20, 2012", 3 pgs.

"European Application Serial No. 06773137.2, Response filed Sep. 18, 2012 to Office Action mailed May 9, 2012", 25 pgs.

"Japanese Application Serial No. 2008-517051, Examiners Decision of Final Refusal mailed Nov. 20, 2012", (w/ English translation), 36 pgs.

"Japanese Application Serial No. 2008-517052, Response filed Jul. 20, 2012 to Office Action mailed May 8, 2012", (w/ English translation), 14 pgs.

"Japanese Application Serial No. 2008-517053, Office Action mailed Aug. 7, 2012", (w/ English translation), 8 pgs.

"Japanese Application Serial No. 2008-517053, Response filed Dec. 20, 2012 to Office Action mailed Aug. 7, 2012", (w/ English translation), 9 pgs.

* cited by examiner

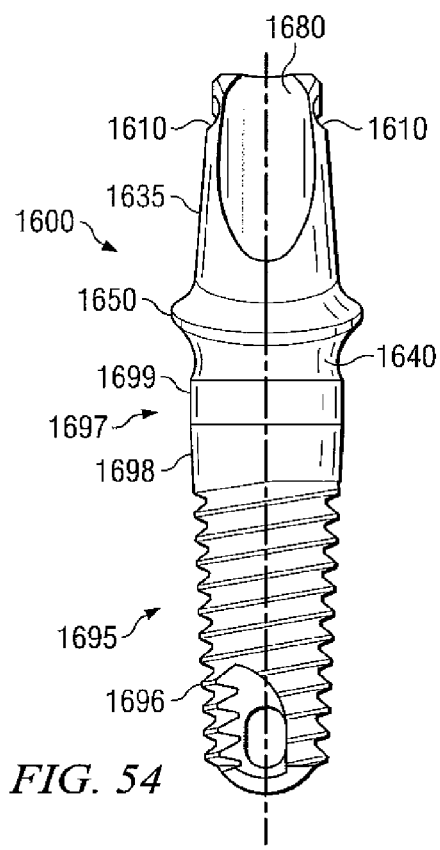
FIG. 54
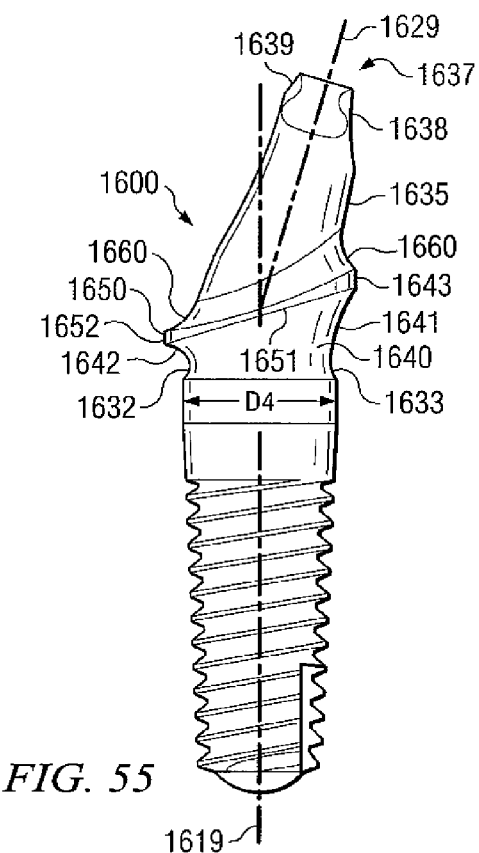
FIG. 55
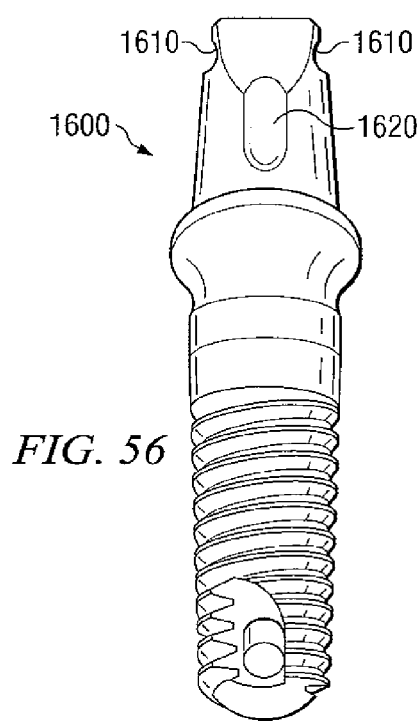
FIG. 56
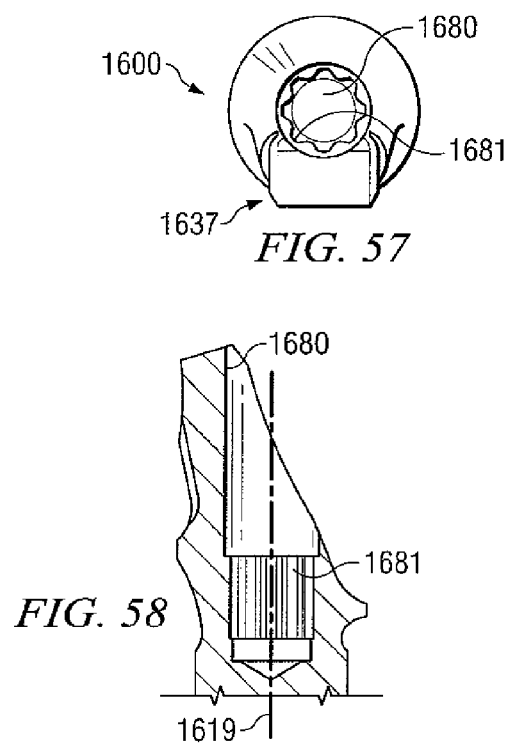
FIG. 57
FIG. 58

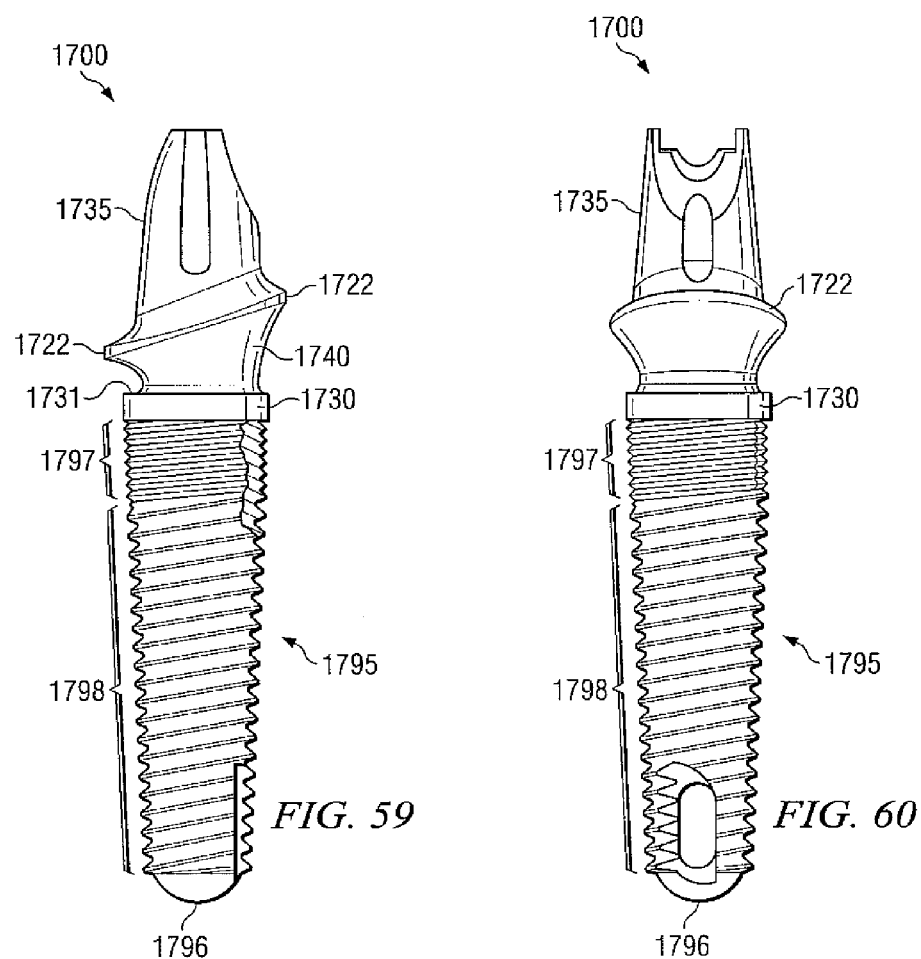

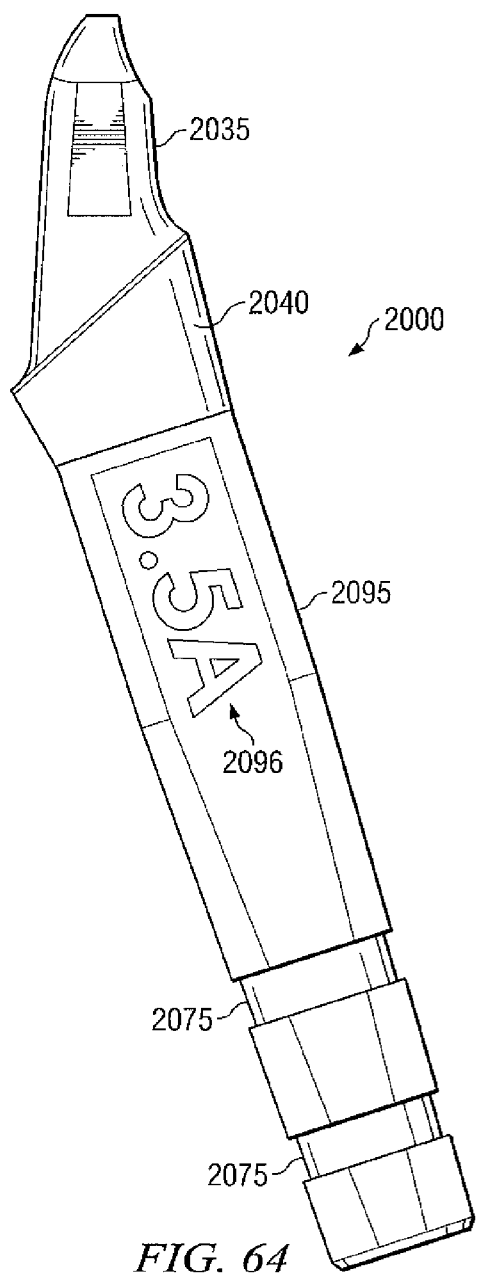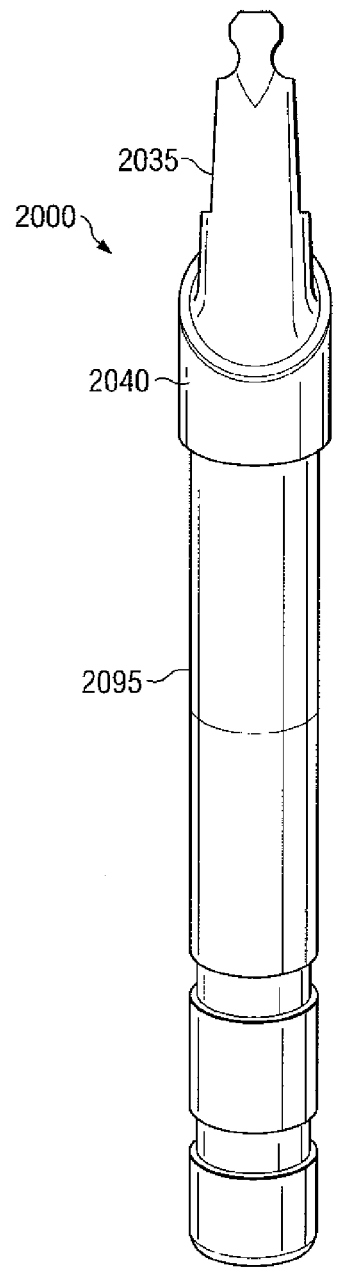
FIG. 64
FIG. 65

DENTAL RESTORATIVE SYSTEM AND COMPONENTS

CROSS-REFERENCE TO RELATED APPLICATIONS

The present application claims the benefit of 35 U.S.C. 119(e) from U.S. Provisional Patent Application Ser. No. 60/691,685, filed Jun. 17, 2005 and entitled "Dental Component System Comprising Abutment and Impression Cap" and U.S. Provisional Patent Application Ser. No. 60/714,641, filed Sep. 7, 2005 and entitled "Dental Component System Comprising Abutment, Unibody Implant and Impression Cap", all hereby incorporated herein by reference for all purposes.

BACKGROUND INFORMATION

The dental art provides various methods and apparatus for compensating for the loss of natural teeth. For example, the natural tooth can be replaced with a prosthetic tooth that is mounted on a unibody implant or a separate abutment secured to an implant. In the instance utilizing a separate implant and abutment, the implant is first installed in the patient's jawbone, typically through threaded engagement. A separate abutment is then secured to the coronal end of the implant and, after sufficient osseointegration of the implant with the patient's jawbone, the prosthetic tooth is secured to the abutment. In a dental restoration involving a unibody or one-piece implant, the implant is installed into the patient's jaw bone and allowed sufficient time to osseointegrate. After this period of time, the prosthetic tooth is installed on the coronal end of the unibody implant.

In the process of performing a dental restoration, it may be desirable to make a model of the patient's mouth to assist in preparing the prosthetic tooth. In such an instance, an impression or transfer coping can be utilized to promote accuracy in the model. An impression coping is placed on an abutment or unibody implant before an impression of the patient's mouth is taken. When the impression material is removed from the patient's mouth, the coping remains in the impression material and is disengaged from the abutment or unibody implant. An analog of the one-piece implant or of an implant and abutment assembly is inserted into the coping that is still engaged in the impression material. Casting material is poured into the impression and around the analog creating a model of the patient's mouth. This allows for an accurate location of the implant or abutment in the patient's mouth and helps to ensure that the prosthetic tooth will fit properly once installed.

SUMMARY OF PREFERRED EMBODIMENTS

Embodiments of the present system are directed toward methods and apparatus for providing a dental restorative system and components, including an abutment, a unibody implant, an impression cap and other components.

BRIEF DESCRIPTION OF THE DRAWINGS

FIG. 54 is a facial view of one embodiment of a component of the system;

FIG. 55 is an interproximal view of the embodiment of FIG. 54;

FIG. 56 is a lingual view of the embodiment of FIG. 54;

FIG. 57 is a coronal view of the embodiment of FIG. 54;

FIG. 58 is a partial section view of the embodiment of FIG. 54;

FIG. 59 is an interproximal view of an alternative embodiment of a system component;

FIG. 60 is a lingual view of the embodiment of FIG. 59;

FIG. 64 is an interproximal view of a component of the system;

FIG. 65 is a facial view of the embodiment of FIG. 64;

DETAILED DESCRIPTION OF THE PREFERRED EMBODIMENTS

Figure 1:
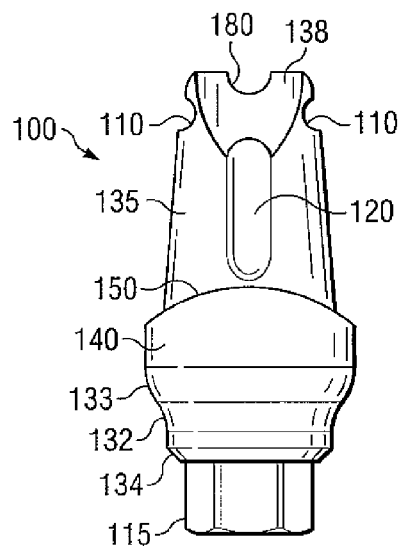
FIG. 1 is a lingual view of one embodiment of a component of the dental component system.

Certain terms are used throughout the following description and claims to refer to particular system features or components. This document does not intend to distinguish between features or components that differ in name but not function.

In the following discussion and in the claims, the terms "including" and "comprising" are used in an open-ended fashion, and thus should be interpreted to mean "including, but not limited to . . . ". Also, the term "coronal" is intended to refer to the portion of a dental implant or component that is distal from the patient's jaw bone or in the direction of the tooth or prosthetic crown furthest from the tooth root after the component has been installed in a patient's mouth. The term "apical" is intended to refer to the portion of a dental implant or component that is proximal to the patient's jaw bone or in the direction of the apex of the tooth root after the device has been installed in a patient's mouth. The terms "facial" or "buccal" (for posterior teeth) are intended to refer to the portion of a dental implant or component that faces outward or away from the patient's tongue, while the term "lingual" is intended to refer to the portion of a dental implant or component that faces inward or toward a patient's tongue. The term "interproximal" is intended to refer to the portion of a dental implant or component that faces an adjacent tooth. The term "emergence profile portion" is intended to refer to the portion of a dental implant or component that extends through a patient's gum tissue. The term "multi-lead thread" is intended to refer to a thread with two or more starting threads at the starting end of a threaded surface (e.g., the apical end of a dental implant).

Referring initially to FIGS. 1-4, an abutment 100 is shown with an emergence profile portion 140 disposed between a polygonal base portion 115 and a tapered post or coronal portion 135. Abutment 100 further comprises an internal longitudinal bore 180 and a margin shoulder 150 disposed between emergence profile portion 140 and tapered coronal portion 135.

Polygonal base portion 115 is configured to mate with and may be frictionally retained by a similarly-shaped recess formed in an implant (not shown). The implant's recess includes a polygonal inner surface including a plurality of generally flat surfaces.

Emergence profile portion 140 comprises a concave surface 132 and a convex surface 133 which extend around the circumference of emergence profile portion 140. Coronal portion 135 further comprises a pair of retention recesses 110 and a longitudinal groove 120. As shown, retention recesses 110 are placed on the outer surface of the coronal end of abutment 100 and transverse to a longitudinal axis 119 of the abutment Although depicted in interproximal aspects of abutment 100, retention recesses 110 may also be disposed on either or both the lingual or buccal aspects. In the embodiment of FIGS. 1-4, longitudinal groove 120 is disposed on the lingual aspect of tapered coronal portion 135; in other embodiments, longitudinal groove 120 may be placed on a facial or interproximal aspect of tapered coronal portion 135.

Concave surface 132 is formed adjacent to a small chamfer 134 and then transitions into a convex surface 133 that is contiguous with concave surface 132. Moving from chamfer 134 toward convex surface 133, concave surface 132 gradually increases in cross-sectional area, therefore providing more room for soft tissue vascularization to promote bone growth near the base of abutment 100 where abutment 100 interfaces with a dental implant. Promoting soft tissue and bone growth in the region adjacent to the outer surface of the emergence profile portion 140 is important because receding tissue can leave a noticeable gap between a crown and adjacent teeth. Increased recession can expose abutment 100 and even the implant, leaving it aesthetically unattractive and potentially vulnerable to disease or infection and even implant failure.

In the embodiment of FIGS. 1-4, concave surface 132 and/or convex surface 133 comprise a variable radius of curvature. By this it is meant that the radius is not constant, but is different at discrete locations along the outer surface of portions 132 and 133. In the embodiment shown, concave surface 132 is 3.5 millimeters in diameter in the area nearest chamfer 134 and convex surface 133 is 4.7 millimeters in diameter in the area adjacent to margin shoulder 150. As described more fully below, other embodiments comprise an emergence profile portion with different diameters and lengths from that shown and described with reference to FIGS. 1-4.

Figure 2:
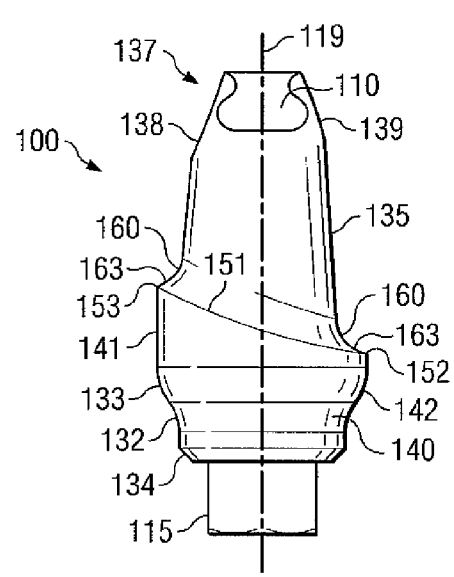
FIG. 2 is an interproximal view of the embodiment of FIG. 1.

As shown in FIG. 2, margin shoulder 150 comprises an arcuate transition zone 160, which extends between the outermost edge of emergency profile portion 140 and tapered coronal portion 140 and tapered coronal portion 135. In this embodiment, transition zone 160 has a variable radius of curvature, meaning that, in the profile view shown in FIG. 2, the radius differs at discrete locations along transition zone 160. Margin shoulder 150 comprises an interproximal aspect 151 that continuously slopes such that the lingual side 153 of margin shoulder 150 extends to a higher point than the facial side 152 of margin shoulder 150 relative to base portion 115. The continuous slope of interproximal aspect 151 includes no positive-to-negative or negative-to-positive changes in slope. Also shown in FIG. 2, the lingual aspect 141 of emergence profile portion 140 has a greater longitudinal length than the facial aspect 142 of emergence profile portion 140. The sloping interproximal aspect 151 may be straight or curved.

Margin shoulder 150 may also comprise a cone portion that is a segment of a true cone. The inclusion of such a cone portion allows for easier dimensional verification for quality assurance purposes during manufacturing because the geometry of such a cone portion is based on a known mathematical formula Therefore, if one point on a cone portion can be established as dimensionally accurate, other points on the cone portion can be verified relatively easily based on the formula that defines the cone portion. Such a cone portion may be located, for example, at location 163 of the margin shoulder. Furthermore, superior geometric control and therefore better tolerance can be maintained using simple shapes such as cones and cylinders versus the more complicated anatomic contours. Enhanced tolerance control allows for an improved fit between the margin section of the abutment or implant and mating transfer coping or other restorative components.

In the embodiment of FIGS. 1-4, longitudinal groove 120 is disposed between margin shoulder 150 and a terminal portion 137 of tapered coronal portion 135. Terminal portion 137 is smaller in cross-section than corresponding regions of coronal portions found on typical prior art abutments (of similar diameter) and comprises a lingual arcuate surface 138 and a facial arcuate surface 139 opposite surface 138. In this manner, arcuate surfaces 138 and 139 may be described as opposing arcuate surfaces.

The reduced size and contoured shape of terminal portion 137 relative to typical abutment posts minimizes the amount of preparation work that a restorative dentist must perform before installing a prosthetic tooth (not shown) on tapered coronal portion 135. One skilled in the art will readily recognize that preparation work on the coronal portion of a dental abutment is typically necessary prior to placement of a prosthetic tooth. Lingual arcuate surface 138 and facial arcuate surface 139 replicate a coronal end that has already been modified by a restorative dentist. In addition, the area of tapered coronal portion 135 near shoulder 150 flares outwardly to provide a base or ledge for a prosthetic tooth to seat against after installation onto abutment 100.

Figure 3:
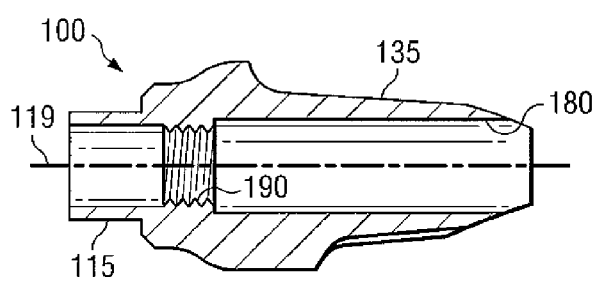
FIG. 3 is a section view of the embodiment of FIG. 1.
Figure 4:
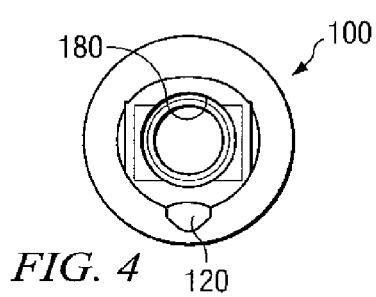
FIG. 4 is a coronal view of the embodiment of FIG. 1.

As shown in the section view of FIG. 3, bore 180 comprises a threaded segment or region 190. Abutment 100 is mounted to an implant (not shown) by inserting polygonal base portion 115 into a corresponding recess in the top of the implant and then inserting a retaining screw (not shown, but see FIGS. 62A, 62B and 62E, for example) into the top of bore 180. The retaining screw first engages threaded region 190 and then engages a threaded bore in the implant, thereby securing abutment 100 to the implant.

Abutment 100 can be manufactured from a variety of biocompatible materials, such as titanium 6ALV4 or ceramic. In addition, portions of abutment 100 (such as emergence profile portion 140) can be anodized or coated with a nitride material such as titanium nitride or another colorizing agent to provide a desired color or other surface property. Titanium nitride coating creates a golden color on the surface of the implant and provides what is generally considered a more aesthetically pleasing appearance than untreated titanium. Portions of abutment 100 can also be treated, coated or roughened to promote soft tissue adhesion or growth in the areas on or adjacent to the treated surfaces.

Figure 5:
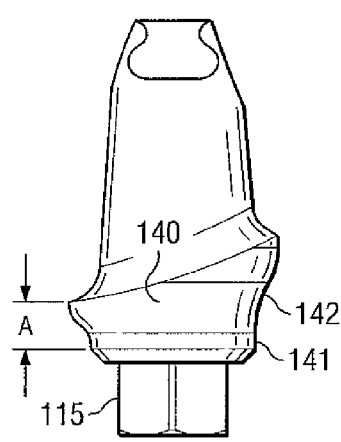
FIG. 5 is an interproximal view of an alternative embodiment of the component of FIGS. 1-4.

While one embodiment is shown in FIGS. 1-4, other embodiments comprise many of the features shown in FIGS. 1-4, but with dimensions that vary from those of the embodiment of FIGS. 1-4. For example, FIG. 5 represents an interproximal view (similar to that shown in FIG. 2) of an alternative embodiment. In the embodiment of FIG. 5, emergence profile portion 140 has a longitudinal length less than that shown in FIG. 2. As a result, lingual aspect 141 and facial aspect 142 do not extend as far from polygonal base 115 in the embodiment of FIG. 5 as compared to the embodiment of FIG. 2. For example, dimension A (sometimes referred to as the "cuff height" and measured parallel to axis 119) is approximately 1 millimeter in the embodiment shown in FIG. 5 and is approximately 2 millimeters in the embodiment shown in FIG. 2.

Figure 6:
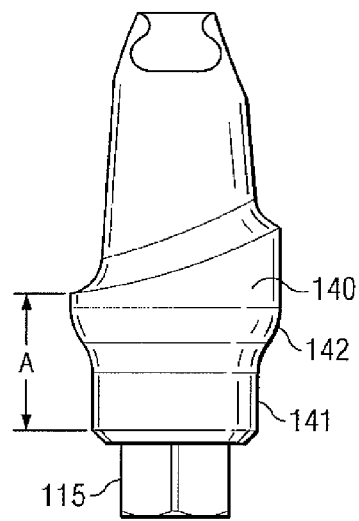
FIG. 6 is an interproximal view of an alternative embodiment of the component of FIGS. 1-4.

FIG. 6 also represents an alternative embodiment to that depicted in FIGS. 1-4. In the embodiment of FIG. 6, emergence profile portion 140 has a longitudinal length greater than that shown in FIG. 2. As a result, lingual aspect 141 and facial aspect 142 extend farther from polygonal base 115 in the embodiment of FIG. 6 as compared to the embodiment of FIG. 2. For example, dimension A is approximately 3 millimeters in the embodiment shown in FIG. 6 while the cuff height of the embodiment shown in FIG. 2 is about 2 millimeters.

Figure 7:
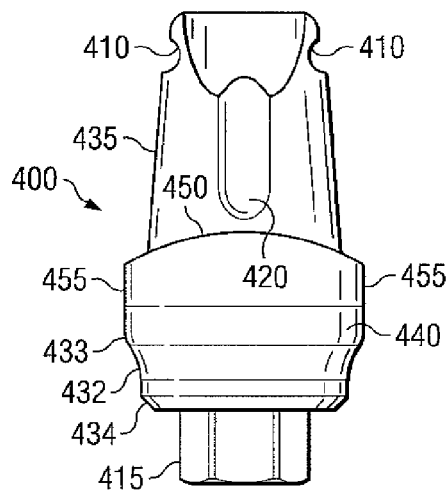
FIG. 7 is a lingual view of one embodiment of a component of the system.
Figure 8:
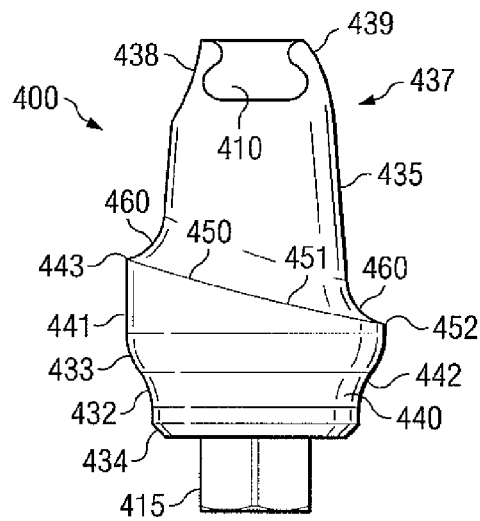
FIG. 8 is an interproximal view of the embodiment of FIG. 7.
Figure 9:
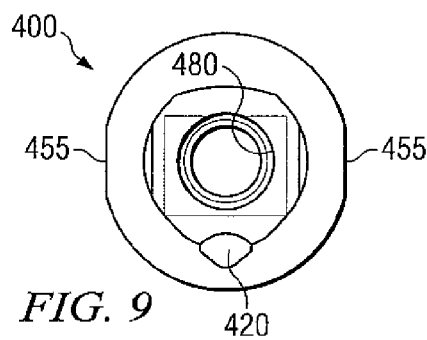
FIG. 9 is a coronal view of the embodiment of FIG. 7.

FIGS. 7-9 depict another embodiment of an abutment that comprises the same general configuration as the embodiments described above. As shown in FIGS. 7-9, an abutment 400 comprises a bore 480, a polygonal base, portion 415, an emergence profile portion 440, and a tapered post or coronal portion 435. Similar to the previously-described embodiments, this embodiment comprises a pair of retention recesses 410, a lingual groove 420 and an emergence profile portion 440 that comprises a concave surface 432 and a convex surface 433.

As shown in FIG. 8, abutment 400 further comprises a margin shoulder 450 with an arcuate transition zone 460, which has a radius of curvature that varies along its length. Margin shoulder 450 comprises an interproximal aspect 451 that slopes such that the lingual side 443 of margin shoulder 450 is higher than the facial side 452 of margin shoulder 450, and such that there are no positive-to-negative or negative-to-positive changes in slope from lingual side 443 to facial side 452. Also shown in FIG. 8, the lingual aspect 441 of emergence profile portion 440 has a greater longitudinal length than the facial aspect 442 of emergence profile portion 440. As previously noted, the sloping interproximal aspect 441 may be straight or curved in profile view.

In this embodiment, tapered post or coronal portion 435 also comprises a terminal portion 437 with a lingual arcuate surface 438 opposing a facial arcuate surface 439. As previously described, terminal portion 437 represents a reduced coronal portion compared to that found on typical, unmodified prior art implants of similar diameter.

As best shown in FIG. 9, abutment 400 includes a pair of flat portions 455 in the upper interproximal region of emergence profile 440. Flat portions 455 allow for more space between adjacent teeth for soft tissue and bone growth in the interproximal region. In the embodiment of FIGS. 7-9, emergence profile portion 440 has a diameter of 4.5 millimeters in the area adjacent to a chamfer 434 and a diameter of 5.5 millimeters in the area below margin shoulder 450 and adjacent to tapered coronal portion 435.

Figure 10:
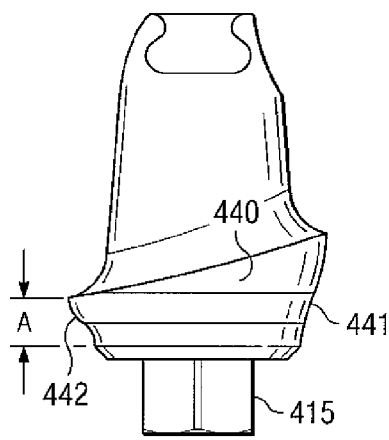
FIG. 10 is an interproximal view of an alternative embodiment of the component of FIGS. 7-9.

Referring now to FIG. 10, an alternative embodiment is shown in the interproximal view (similar to that shown in FIG. 8). In the embodiment of FIG. 10, emergence profile portion 440 has a longitudinal length less than that of the embodiment shown in FIG. 8. As a result, lingual aspect 441 and facial aspect 442 do not extend as far from polygonal base 415 in the embodiment of FIG. 10 as compared to the embodiment of FIG. 8. For example, dimension A is approximately 1 millimeter in the embodiment shown in FIG. 10 while the cuff height is approximately 2 millimeters in the embodiment shown in FIG. 8.

Figure 11:
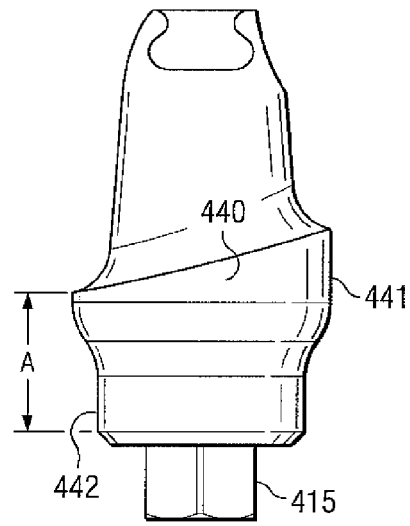
FIG. 11 is an interproximal view of an alternative embodiment of the component of FIGS. 7-9.

FIG. 11 also represents an alternative embodiment to that depicted in FIGS. 7-9. In the embodiment of FIG. 11, emergence profile portion 440 has a longitudinal length greater than that shown in FIG. 8. As a result, lingual aspect 441 and facial aspect 442 extend farther from polygonal base 415 in the embodiment of FIG. 11 as compared to the embodiment shown in FIG. 8. For example, dimension A is approximately 3 millimeters in the embodiment shown in FIG. 11 while the cuff height is approximately 2 millimeters in the embodiment shown in FIG. 8.

Figure 12:
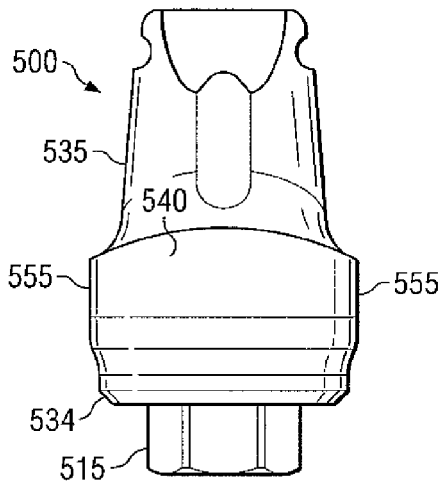
FIG. 12 is a lingual view of one embodiment of a component of the system.
Figure 13:
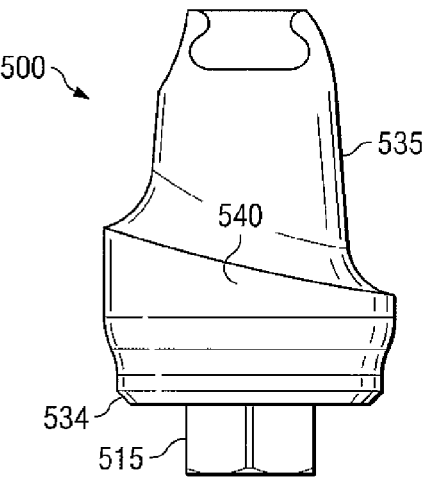
FIG. 13 is an interproximal view of the embodiment of FIG. 12.
Figure 14:
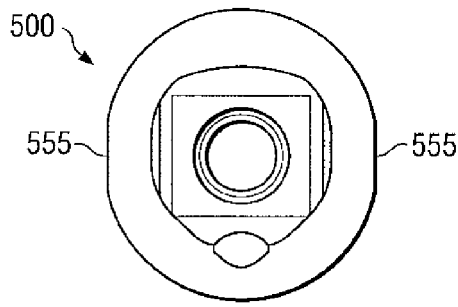
FIG. 14 is a coronal view of the embodiment of FIG. 12.

FIGS. 12-14 depict another abutment embodiment that comprises the same general configuration as the embodiments described above. However, in the embodiment of FIGS. 12-14, abutment 500 comprises an emergence profile portion 540 with a diameter of 5.7 millimeters in the area adjacent to a chamfer 534 and a diameter of 6.5 millimeters in the area below margin shoulder 550 and adjacent to tapered post or coronal portion 535. The embodiment shown in FIGS. 12-14 comprises a polygonal base portion 515, an emergence profile portion 540, and a tapered coronal portion 535. This embodiment also comprises a pair of flat portions 555 in the upper interproximal region of emergence profile 540.

Figure 15:
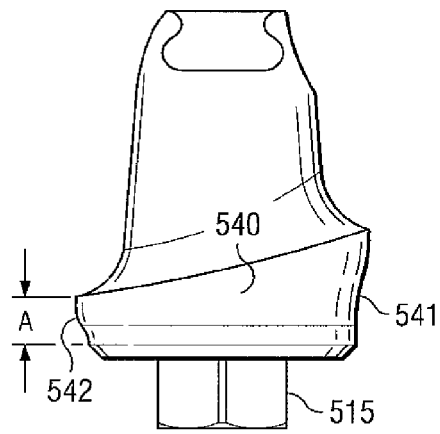
FIG. 15 is an interproximal view of an alternative embodiment of the component of FIGS. 12-14.

Referring now to FIG. 15, an alternative embodiment is shown in the interproximal view (similar to that shown in FIG. 13). In the embodiment of FIG. 15, emergence profile portion 540 has a longitudinal length less than that shown in FIG. 13. As a result, a lingual aspect 541 and a facial aspect 542 do not extend as far from polygonal base 515 in the embodiment of FIG. 15 as compared to the embodiment of FIG. 13. For example, dimension A is approximately 1 millimeter in the embodiment shown in FIG. 15 while the cuff height is approximately 2 millimeters in the embodiment shown in FIG. 13.

Figure 16:
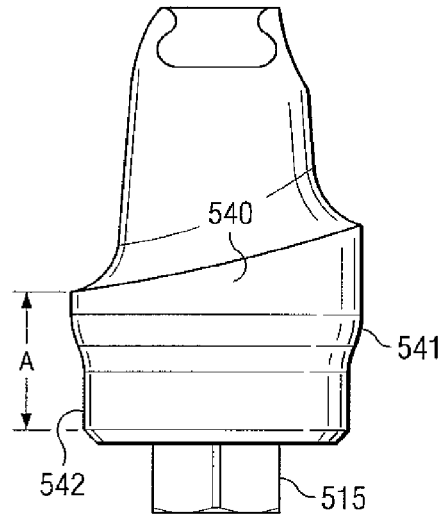
FIG. 16 is an interproximal view of an alternative embodiment of the component of FIGS. 12-14.

FIG. 16 also represents an alternative embodiment to that depicted in FIGS. 12-14. In the embodiment of FIG. 16, emergence profile portion 540 has a longitudinal length greater than that shown in FIG. 13. As a result, lingual aspect 541 and facial aspect 542 extend farther from polygonal base 515 in the embodiment of FIG. 15 as compared to the embodiment shown in FIG. 13. For example, dimension A is approximately 3 millimeters in the embodiment shown in FIG. 16 while the cuff height is approximately 2 millimeters in the embodiment shown in FIG. 13.

Figure 17:
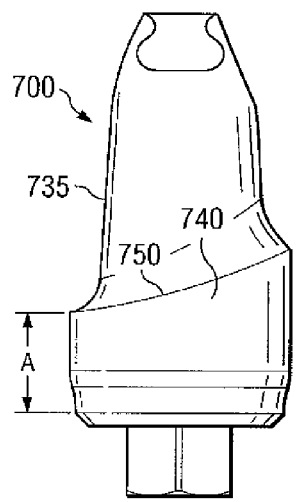
FIG. 17 is an interproximal view of one embodiment of a component of the system.
Figure 18:
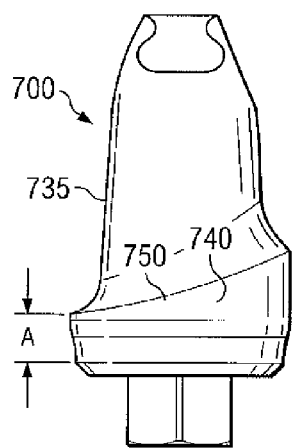
FIG. 18 is an interproximal view of an alternative embodiment of the component of FIG. 17.
Figure 19:
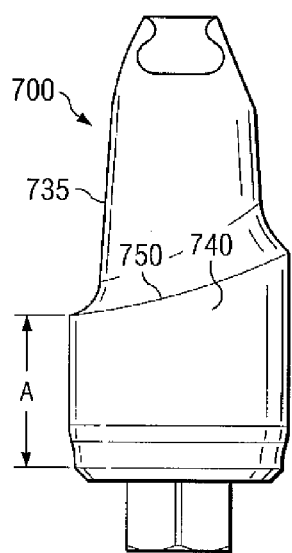
FIG. 19 is an interproximal view of an alternative embodiment of the component of FIG. 17.

Alternative abutments 701-703 are depicted in FIGS. 17-19, respectively. Each abutment 701-703 comprises a tapered coronal portion 735 and margin shoulder 750 that have the same general configuration as the previously described embodiments. However, the embodiments shown in FIGS. 17-19 comprise an emergence profile portion 740 that is generally cylindrical and does not comprise a concave and convex surface shown in the previous embodiments. While the embodiments of FIGS. 17-19 comprise an emergence profile portion 740 that is 4.5 millimeters in diameter at all locations along the cylindrical surface of section 740, other embodiments may comprise emergence profile portions having other diameters. As shown, the embodiments of FIGS. 17-19 comprise emergence profile portions 740 that are different longitudinal lengths, so that dimension A is approximately 1 millimeter for abutment 701 in FIG. 18, 2 millimeters for abutment 702 in FIG. 17, and 3 millimeters for abutment 703 in FIG. 19. Other embodiments may comprise different length emergence profile portions.

Figure 20:
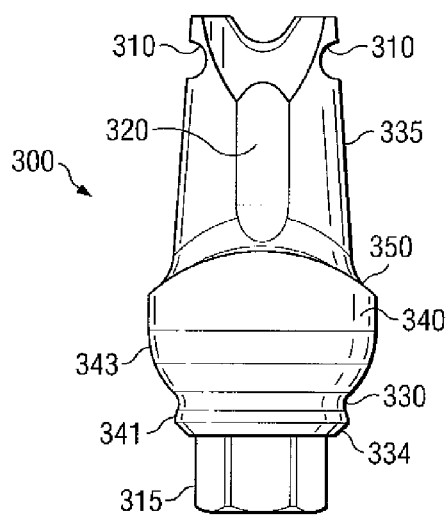
FIG. 20 is a lingual view of one embodiment of a component of the system.
Figure 21:
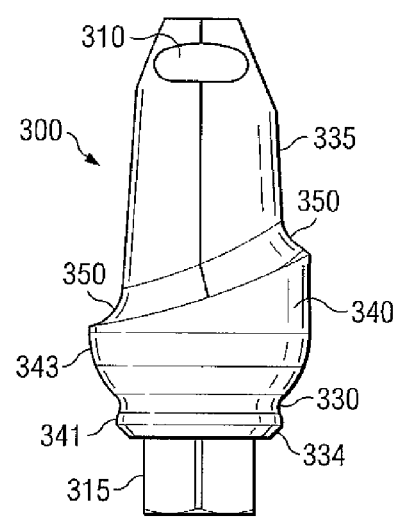
FIG. 21 is an interproximal view of the embodiment of FIG. 20.
Figure 22:
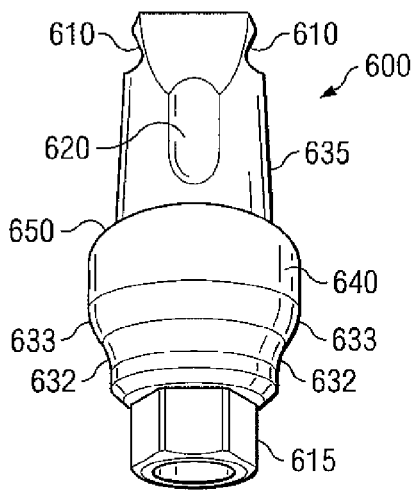
FIG. 22 is a lingual view of one embodiment of a component of the system.

Another alternative embodiment is shown in FIGS. 20 and 21, wherein abutment 300 comprises a polygonal base portion 315, a chamfer 334, an emergence profile portion 340 and a tapered coronal portion 335. Abutment 300 comprises a pair of retention recesses 310 and a longitudinal groove 320 as previously described. In this embodiment, the base of emergence profile portion 340 comprises a lower convex surface 341 that is disposed between a concave surface 330 and chamfer 334. Emergence profile portion 340 further comprises an upper convex surface 343 between concave surface 330 and a margin shoulder 350. As shown in FIGS. 20 and 21, lower convex surface 341 comprises a radius of curvature that is less than the radius of curvature of upper convex surface 343. Compared, for example, to abutment 100 shown and described with reference to FIGS. 1-4, concave surface 330 allows for even more room for soft tissue and bone growth around abutment 300. Concave surface 330 may be incorporated on abutments of varying configurations (including different diameters, lengths, or post angles). Thus, the cross-sectional diameter of the abutment 300 is less in the concave region 330 than the widest extent of the portion of the abutment 300 located apically with respect to the concave region 330 (i.e. below concave region 330 as shown in FIG. 20). This creates a recess in the transgingival surface of the abutment 300.

Another alternative embodiment is shown in FIGS. 22-26 as abutment 600, comprising a polygonal base portion 615, an emergence profile portion 640, and a tapered post or coronal portion 635. Similar to the previously-described embodiments, this embodiment comprises a pair of retention recesses 610, a lingual groove 620, and an emergence profile portion 640 that comprises a concave surface 632 and a convex surface 633. In addition, a margin shoulder 650 is disposed between emergence profile portion 640 and tapered coronal portion 635. Comparable to the embodiment shown in FIGS. 1-4, the embodiment of FIGS. 22-26 comprise an emergence profile portion that increases from about 3.5 millimeters to about 4.5 millimeters in diameter and has a cuff height (shown as dimension A in FIG. 25) of approximately 2 millimeters.

In this embodiment, tapered coronal portion 635 also comprises a terminal portion 637 with a lingual arcuate surface 638 opposing a facial arcuate surface 639. Terminal portion 637 is a reduced upper coronal portion, as shown in FIGS. 22-26.

Figure 23:
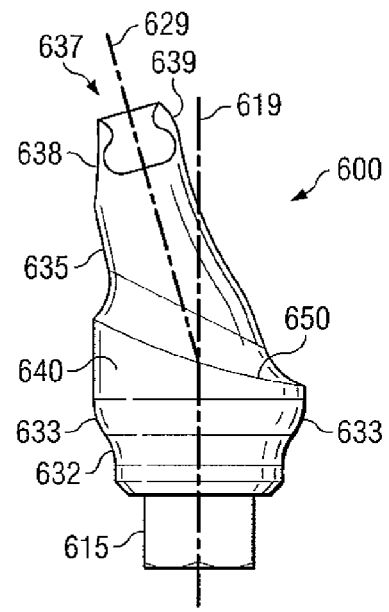
FIG. 23 is an interproximal view of the embodiment of FIG. 22.

As shown in FIG. 23, unlike previously described embodiments, tapered coronal portion 635 comprises a center axis 629 that is not parallel with a longitudinal axis 619 that passes through the center of base portion 615 and emergence profile portion 640. In this embodiment, center axis 629 is set an angle of 17 degrees from longitudinal axis 619. In other embodiments, center axis 629 is set an angle other than 17 degrees. Abutment 600 thus may be described as an angled abutment with post 635 being angled relative to base portion 615 and axis 619.

Figure 25:
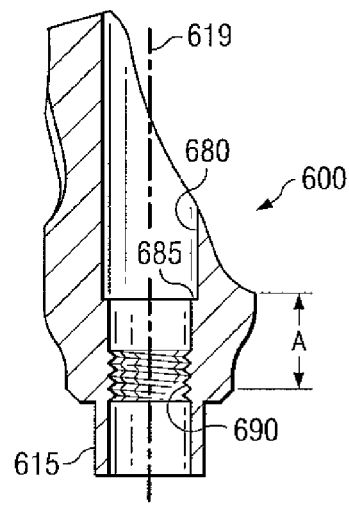
FIG. 25 is a section view of the embodiment of FIG. 22.
Figure 24:
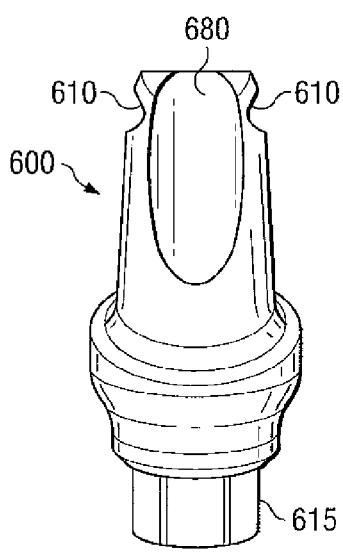
FIG. 24 is a facial view of the embodiment of FIG. 22.
Figure 26:
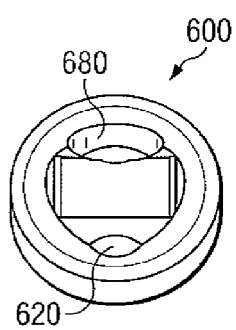
FIG. 26 is a coronal view of the embodiment of FIG. 22.

As shown in the section view of FIG. 25, abutment 600 comprises a bore 680 that is parallel with and preferably coaxially aligned with longitudinal axis 619. Bore 680 further comprises a threaded segment or portion 690 and a shoulder 685 that engages the head of a retaining screw (not shown) used to secure abutment 600 to an implant.

Figure 27:
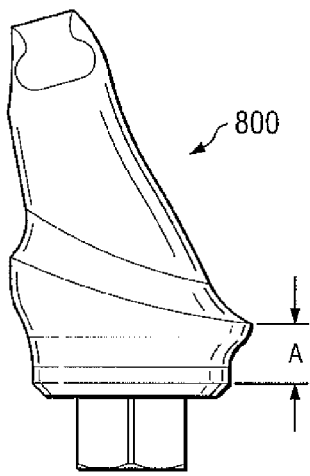
FIG. 27 is an interproximal view of an alternative embodiment of the component of FIGS. 22-26.
Figure 28:
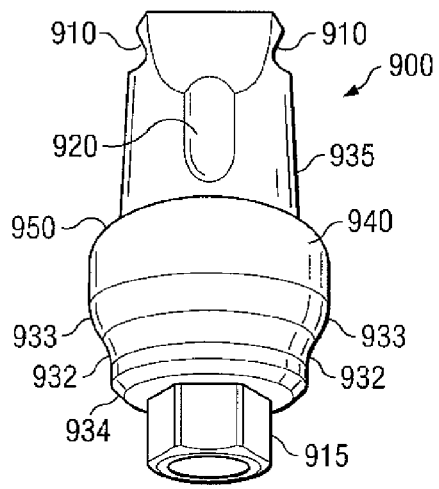
FIG. 28 is a lingual view of one embodiment of a component of the system.

An alternative embodiment is shown in FIG. 27 as abutment 800, which comprises the same general configuration as abutment 600 shown in FIGS. 22-26. However, dimension A for abutment 800 is about 1 millimeter instead of a cuff height of 2 millimeters in the embodiment of FIGS. 22-26.

Figure 29:
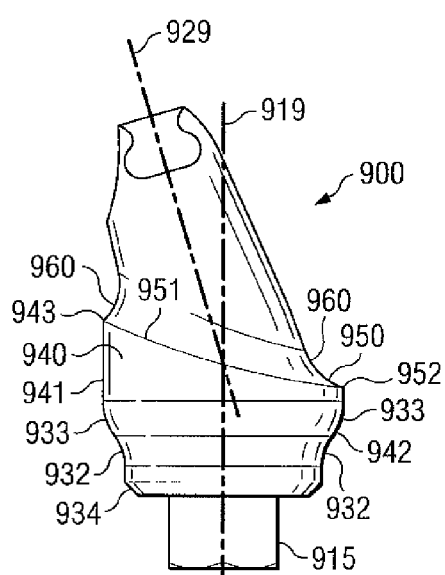
FIG. 29 is an interproximal view of the embodiment of FIG. 28.

Another alternative embodiment is shown in FIGS. 28-31 as abutment 900, comprising a bore 980, a polygonal base portion 915, an emergence profile portion 940, and a tapered coronal portion 935. The embodiment of FIGS. 28-31 also comprises a pair of retention recesses 910 and a lingual groove 920 and an emergence profile portion 940 that comprises a concave surface 932 and a convex surface 933. As shown in FIG. 29, abutment 900 further comprises margin shoulder 950 with an arcuate transition zone 960, which comprises a radius of curvature that is not uniform, but instead varies along its profile. Margin shoulder 950 comprises an interproximal aspect 951 that slopes such that a lingual side 943 of margin shoulder 950 is higher than a facial side 952 of margin shoulder 950. Also shown in FIG. 29, a lingual aspect 941 of emergence profile portion 940 has a greater longitudinal length than a facial aspect 942 of emergence profile portion 940. Similar to the previously-described embodiment of FIGS. 22-26, tapered coronal portion 935 comprises a center axis 929 that is disposed at an angle of 17 degrees from a longitudinal axis 919 of base portion 915 and emergence profile portion 940.

In the embodiment of FIGS. 28-31, emergence profile portion 940 has a diameter of 4.5 millimeters in the area adjacent to a chamfer 934 and a diameter of 5.5 millimeters in the area adjacent to tapered coronal portion 935.

Figure 30:
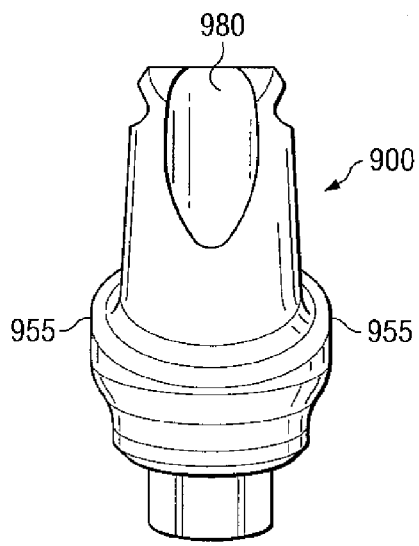
FIG. 30 a facial view of the embodiment of FIG. 28.
Figure 31:
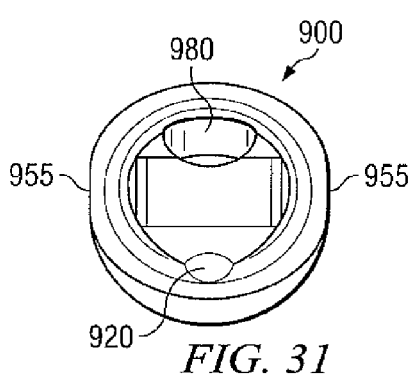
FIG. 31 is a coronal view of the embodiment of FIG. 28.

Abutment 900 also comprises a pair of flat portions 955 in the upper interproximal region of emergence profile 940, as best shown in FIGS. 30 and 31. Flat portions 955 allow for more space between teeth for soft tissue and bone growth in the interproximal region.

Figure 32:
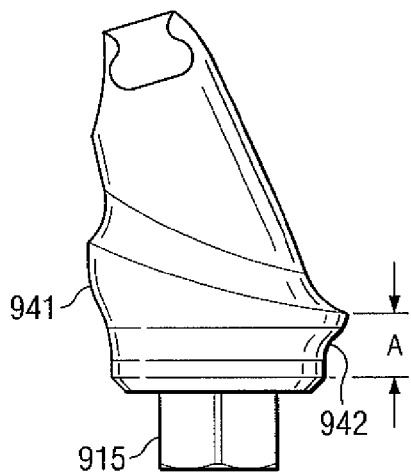
FIG. 32 is an interproximal view of an alternative embodiment of the component of FIGS. 28-31.
Figure 33:
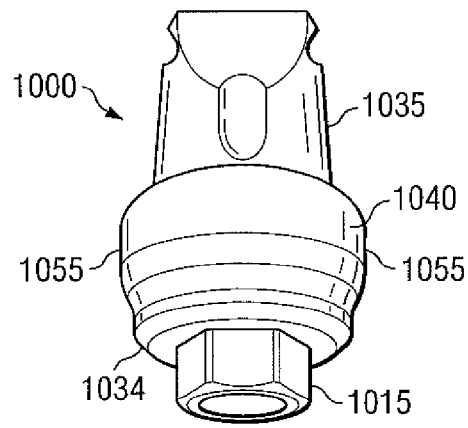
FIG. 33 is a lingual view of one embodiment of a component of the system.

Referring now to FIG. 32, an alternative embodiment is shown in the interproximal view (similar to that shown in FIG. 29) The emergence profile portion 940 of abutment 900 of FIG. 32 has a longitudinal length less than that of the abutment shown in FIG. 29. As a result, lingual aspect 941 and facial aspect 942 do not extend as far from polygonal base 915 in the embodiment of FIG. 32 as compared to the embodiment of FIG. 29. For example, dimension A is approximately 1 millimeter in the embodiment shown in FIG. 32 while the cuff height is approximately 2 millimeters in the embodiment shown in FIG. 29.

FIGS. 33-36 depict still another abutment embodiment that comprises the same general configuration as the embodiment of FIG. 28-31. In the embodiment shown in FIGS. 33-36, an abutment 1000 comprises bore 1080, a polygonal base portion 1015, an emergence profile portion 1040, and a tapered coronal portion 1035. Similar to the embodiment of FIGS. 28-31, tapered coronal portion or post 1035 comprises a center axis 1029 that is set an angle of 17 degrees from a longitudinal axis 1019 of base portion 1015 and emergence profile portion 1040. This embodiment also comprises a pair of flat portions 1055 in the upper interproximal region of emergence profile 1040. However, in the embodiment of FIGS. 33-36, abutment 1000 comprises an emergence profile portion 1040 with a diameter of 5.7 millimeters in the area adjacent to a chamfer 1034 and a diameter of 6.5 millimeters in the area adjacent to tapered coronal portion 1035.

Figure 34:
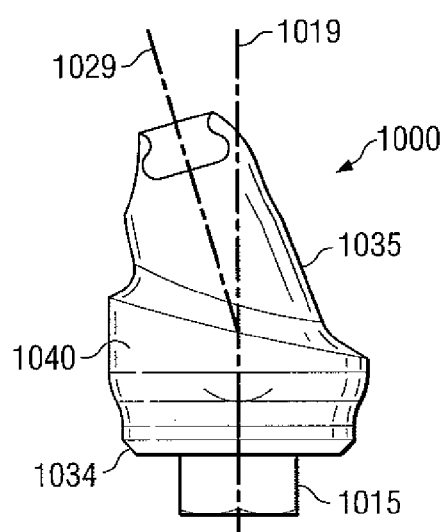
FIG. 34 is an interproximal view of the embodiment of FIG. 33.
Figure 35:
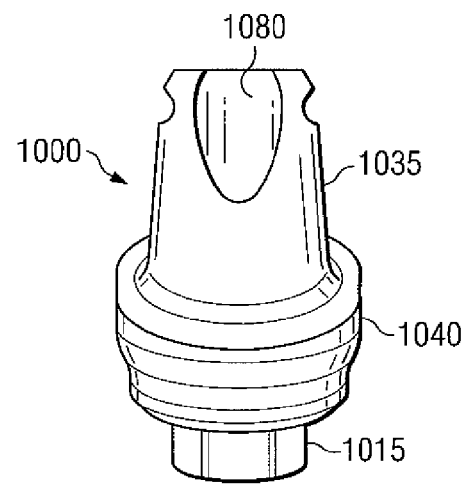
FIG. 35 is a facial view of the embodiment of FIG. 33.
Figure 36:
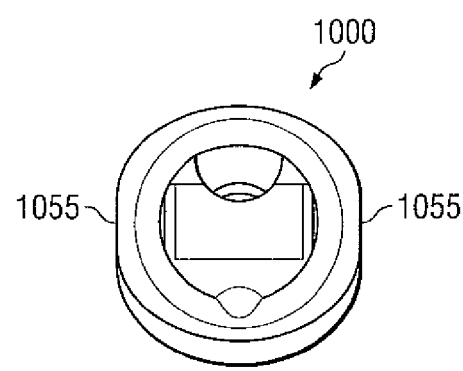
FIG. 36 is a coronal view of the embodiment of FIG. 33.
Figure 37:
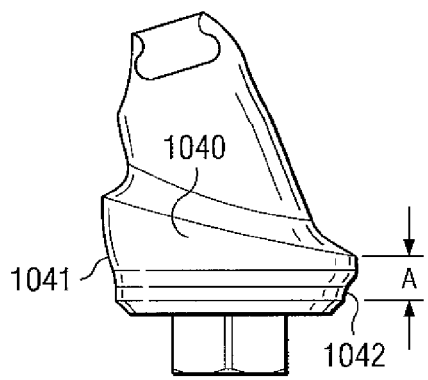
FIG. 37 is an interproximal view of an alternative embodiment of the component of FIGS. 33-36.

Referring now to FIG. 37, an alternative embodiment is shown in the interproximal view (similar to that shown in FIG. 34). In the embodiment of FIG. 37, emergence profile portion 1040 of abutment 1000 has a longitudinal length less than that shown in FIG. 34. As a result, lingual aspect 1041 and facial aspect 1042 do not extend as far from polygonal base 1015 in the embodiment of FIG. 37 as compared to the embodiment of FIG. 34. For example, dimension A is approximately 1 millimeter in the embodiment shown in FIG. 37 while the cuff height is approximately 2 millimeters in the embodiment shown in FIG. 34.

Figure 38:
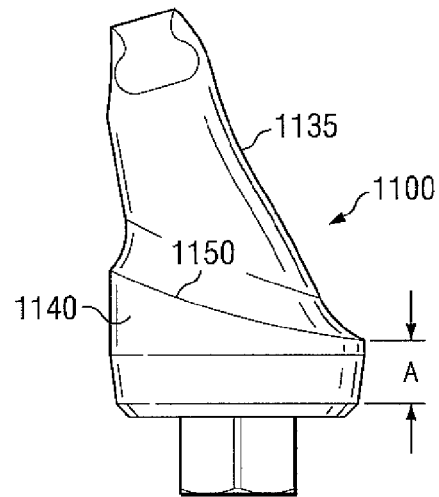
FIG. 38 is a lingual view of an alternative embodiment of a component of the system.
Figure 39:
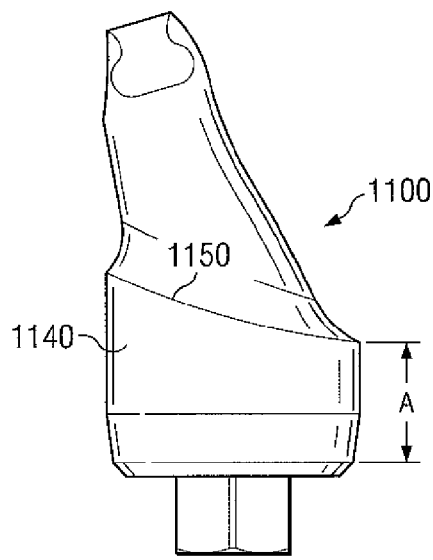
FIG. 39 is a lingual view of an alternative embodiment of the component of FIG. 38.

Yet other alternative embodiments of an abutment 1100 are also depicted in FIGS. 38 and 39. Abutment 1100 comprises a tapered coronal portion 1135 and margin shoulder 1150 having the same general configurations as the previously described embodiments. However, the embodiments shown in FIGS. 38 and 39 comprise an emergence profile portion 1140 that includes generally cylindrical outer surfaces extending between margin 1150 and chamfer 1134 and does not comprise a concave and convex surface shown in previous embodiments. While the embodiments of FIGS. 38-39 comprise an emergence profile portion 1140 that is 4.5 millimeters in diameter, other embodiments may comprise different diameter emergence profile portions. As shown, the embodiments of FIGS. 38 and 39 comprise emergence profile portions 1140 that are different lengths, so that dimension A is approximately 1 millimeter in FIG. 38 and 2 millimeters in FIG. 39. Other embodiments may comprise different length emergence profile portions.

As demonstrated above, embodiments of the present invention comprise abutments with a number of different configurations. Dimensions such as the emergence profile diameter and length, and angle (if any) between the tapered coronal portion and the emergence profile portion can be varied to match the needs of an individual patient. Factors such as the amount of space available and the orientation of the implant will influence the doctor's decision on which abutment to select when performing a tooth restoration on a patient.

Figure 40:
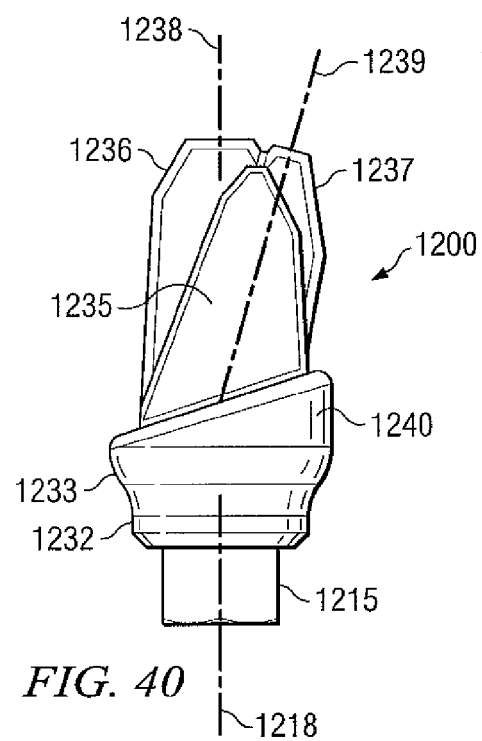
FIG. 40 is an interproximal view of a component of the system.
Figure 41:
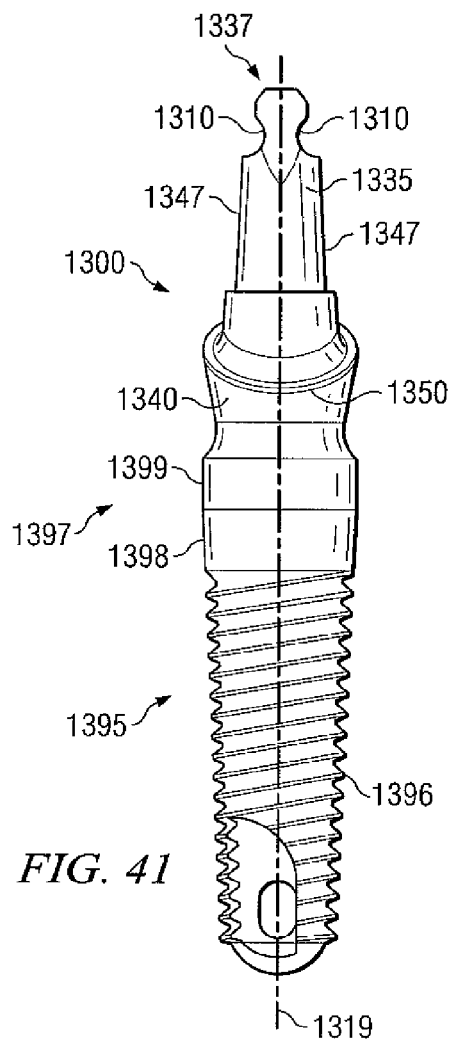
FIG. 41 is a facial view of one embodiment of a component of the system.

To assist in determining whether a straight or an angled abutment should be selected, a doctor may employ a fitting abutment for a trial fitting. As shown in FIG. 40, a fitting abutment 1200 comprises a polygonal base portion 1.215 with a longitudinal axis 1218 and an emergence profile portion 1240 with a concave surface 1232 and a convex surface 1233. However, instead of a tapered coronal portion similar to those shown in previous embodiments, fitting abutment 1200 comprises a coronal portion 1235 that comprises a straight peak 1236 with a longitudinal axis 1238 and an angled peak 1237 with a longitudinal axis 1239. Longitudinal axis 1238 is generally parallel and coaxial with longitudinal axis 1218, while longitudinal axis 1239 is angled from, and not parallel to, longitudinal axis 1218. Straight peak 1236 replicates the location of a post of a permanent straight abutment, while angled peak 1237 replicates the location of the post of a permanent angled abutment. This allows a doctor to place fitting abutment 1200 at the site in the patient's mouth where the restoration will be placed and determine if a straight or angled abutment will provide the best fit. Fitting abutment 1200 may be manufactured in various diameters and lengths to assist the doctor in determining the proper size as well. Fitting abutment 1200 may be made of a material, such as plastic, that is less expensive than titanium or other material typically used for permanent abutments.

Other embodiments of the present invention comprise a unibody, or one-piece, implant structure that includes a bone-engaging foundation portion and an abutment portion integral therewith for mounting the prosthesis, as distinguished from the assembly having an abutment member or component that may be secured to a separate bone engaging implant member. One such embodiment is shown in FIGS. 41-44, which comprises a unibody implant 1300 with an emergence profile portion 1340 disposed between body portion 1395 and tapered coronal portion or post 1335. Unibody implant 1300 further comprises a margin shoulder 1350 between emergence profile portion 1340 and tapered coronal portion 1335.

Tapered coronal end 1335 comprises a pair of flats 1347, a longitudinal groove 1320 and a terminal portion 1337 with a pair of retention recesses 1310 transverse to a longitudinal axis 1319. In this embodiment, flats 1347 and retention recess 1310 are shown in an interproximal position and longitudinal groove 1320 is shown in a lingual position, but alternative embodiments may comprise flats or grooves in alternate locations. Flats 1347 may be used to rotate implant 1300, by engagement with a rotating tool, to assist in threadably engaging implant 1300 with a patient's bone during installation of implant 1300. In the embodiment shown in FIGS. 41-44, tapered coronal portion 1335 is free from having a longitudinal bore, as this embodiment is intended to be used to mount cement-retained prostheses or in configurations where the cross-sectional area of the tapered coronal portion is not sufficient to include an internal bore.

Terminal portion 1337, comprising a lingual arcuate surface 1338 opposing a facial arcuate surface 1339, embodies a reduced coronal end compared to those of typical, unmodified prior art abutments having similar diameters.

The reduced size of terminal portion 1337 minimizes the amount of preparation work that a restorative dentist must perform before installing a prosthetic tooth (not shown) on tapered coronal portion 1335 as has been previously described. Minimizing necessary preparation to a one-piece implant is particularly important because preparations are performed in the mouth. Debris and heat generated during preparation can negatively affect tissue health and even cause implant failure. Lingual arcuate surface 1338 and facial arcuate surface 1339 also replicate the appearance of an end that has already been modified by a restorative dentist or surgeon. In addition, the area of tapered coronal portion 1335 near margin shoulder 1350 flares outwardly to provide a base or ledge for a prosthetic tooth to seat against after installation onto implant 1300.

Figure 42:
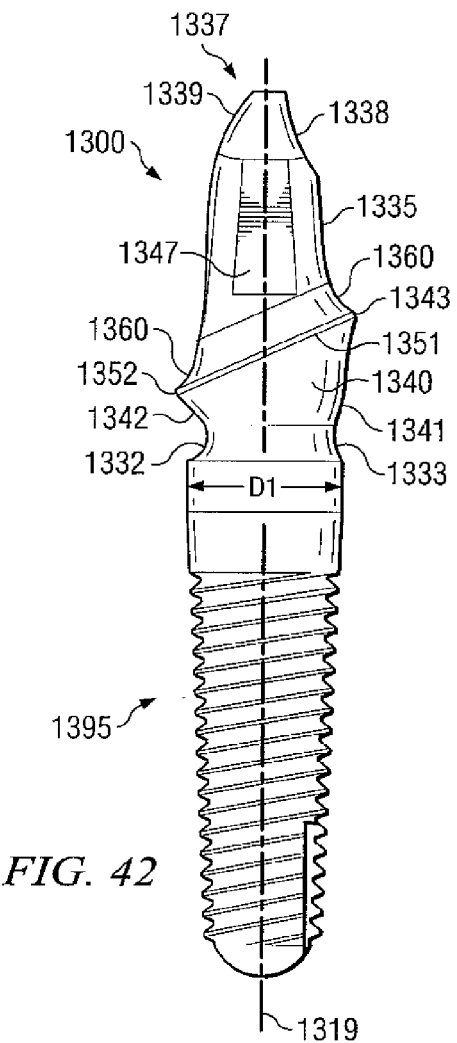
FIG. 42 is an interproximal view of the embodiment of FIG. 41.
Figure 43:
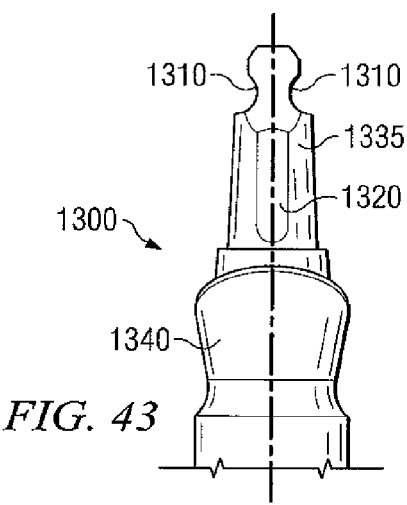
FIG. 43 is a partial lingual view of the embodiment of FIG. 41.
Figure 44:
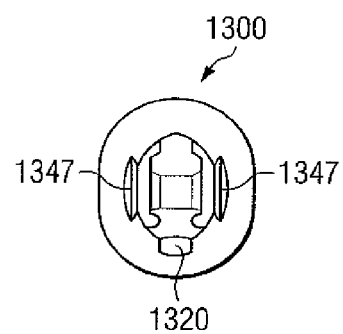
FIG. 44 is a coronal view of the embodiment of FIG. 41.
Figure 45:
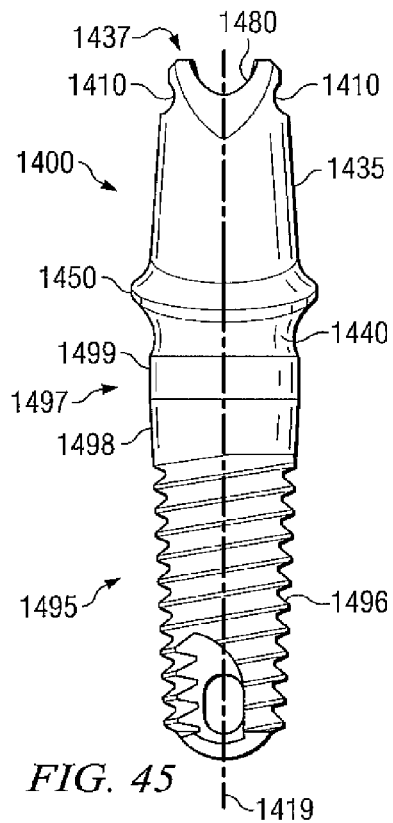
FIG. 45 is a facial view of one embodiment of a component of the system.

As shown in FIG. 42, margin shoulder 1350 is disposed between tapered coronal portion 1335 and emergence profile portion 1340. Margin shoulder 1350 comprises an arcuate transition zone 1360, which may have a radius of curvature that varies along the length of the zone's profile. Margin shoulder 1350 further comprises an interproximal aspect 1351 that continuously slopes such that a lingual side 1343 of margin shoulder 1350 is higher than a facial side 1352 of margin shoulder 1350. Also shown in FIG. 42, a lingual aspect 1341 of emergence profile portion 1340 has a greater longitudinal length than a facial aspect 1342 of emergence profile portion 1340. The margin shoulder 1350, as well as the other margin shoulders described throughout, may be curved or straight as is shown in the various embodiments illustrated herein.

In addition, adjacent to body portion 1395, emergence profile portion 1340 comprises a facial concave surface 1332 and a lingual concave surface 1333. As previously described, concave surfaces 1332 and 1333 provide more room for soft tissue vascularization to promote bone growth, improving aesthetics and reducing the likelihood of infection. As shown in FIG. 42, concave surfaces 1332 and 1333 extend within an outer envelope diameter D1 of upper threaded body portion 1395. Outer envelope diameter D1 is the maximum envelope diameter of body portion 1395. Concave surfaces 1332 and 1333 may comprise various configurations other than that shown in FIGS. 41-44. For example, concave surfaces 1332 and 1333 may comprise either multiple or a single radius of curvature and may extend different depths into emergence profile portion 1340. In addition, the center of curvature for concave surface 1332 may be located either within outer envelope diameter D1 or outside of outer envelope diameter D1. In the embodiment of FIGS. 41-44, lingual concave surface 1333 has a greater radius of curvature than facial concave surface 1332, and facial concave surface 1332 extends farther into emergence profile portion 1340 than does lingual concave surface 1333. Concave surface 1332 therefore creates a recess in the emergence region.

As shown in the embodiment of FIGS. 41-44, body portion 1395 comprises a threaded portion 1396 and a non-threaded collar portion 1397. Collar portion 1397 comprises a tapered section 1398 having a generally frustoconical surface and a cylindrical section 1399. In certain embodiments, threaded portion 1396 is tapered and comprises multiple-lead threads such as double-lead or triple-lead threads, and non-threaded collar portion 1397 comprises a roughened surface.

The use of multiple lead threads allows implant 1300 to be fully inserted into a patient's jaw bone with fewer rotations than if a single lead thread were utilized This reduces the amount of time it takes to insert implant 1300, and thereby decreases patient discomfort and lowers risks by reducing operation time. In yet another aspect of an embodiment, a series of markers such as colored dots or etched portions of threads (not shown) are placed on threaded portion 1396 to indicate how far implant 1300 has been inserted into a patient's jaw bone. This feature allows a person inserting implant 1300 to know how far implant 1300 has been inserted into the patient's jaw bone and reduces the risk of inserting implant 1300 improperly.

Implant 1300 can be manufactured from a variety of biocompatible materials, such as titanium 6ALV4, ceramic, polymer or polymer composite, or combinations thereof. For example, the abutment portion can be ceramic or polymer composite and the implant portion can be titanium. In addition, portions of implant 1300 (such as emergence profile portion 1340) can be anodized or coated with a material such as titanium nitride or another colorizing agent to provide a desired color or other surface property. Portions of implant 1300 can also be treated with a coating that comprises a roughening agent to increase the surface roughness.

In another aspect of embodiments of the present system, portions of implant 1300 can be textured through various methods such as microtexturing or chemical etching. Increasing the surface roughness of implant 1300 also increases the surface area and thereby promotes osseointegration and soft tissue growth around implant 1300. In one embodiment, a first process such as microtexturing is used to increase the surface roughness on the apical portions of implant 1300, while a second process such as chemical etching is used increase the surface roughness of the coronal portions of the implant. In this embodiment, the surface finish of the apical portions of the implant is rougher than the surface finish of the coronal portions. In other embodiments, a second mechanical blasting process (with a medium that is less aggressive than that used in microtexturing) is used to increase the surface roughness of the coronal portions instead of chemical etching.

In one embodiment, a portion of implant 1300 is microtextured by blasting the implant with hydroxyapatite particles and another portion is etched with diluted hydrochloric acid (HCl). In this embodiment, 5 mole weight HCl is diluted with water by a 20:1 ratio and then used to chemically etch portions of implant 1300.

Another embodiment of a unibody implant is shown in FIGS. 45-49 as implant 1400. Similar to the embodiment of FIGS. 41-44, this embodiment comprises an emergence profile portion 1440 disposed between body portion 1495 and a tapered coronal portion 1435. Unibody implant 1400 further comprises a margin shoulder 1450 between emergence profile portion 1440 and tapered coronal portion 1435.

Unibody implant 1400 comprises the same general configuration as implant 1300, but tapered coronal portion 1435 also incorporates an internal bore 1480 with a tool-engaging feature 1481 that may be used to rotate implant 1400 and assist in threadably engaging implant 1400 into a patient's jaw bone. The larger size of the coronal portion provides adequate material for the bore and tool engaging feature. Including the bore allows a common drive tool to be used: the geometry of external flats may vary with the external geometry of the tapered portion, but internal geometry may be held constant regardless of the geometry of the tapered portion. In the embodiment shown in FIGS. 48 and 49, tool-engaging feature 1481 is a segment of internal bore 1480 formed to have a polygonal cross section or other non circular cross section, such as any shape having one or more flats. While the embodiment of FIGS. 45-49 does not comprise flats on the outer surface of post 1435 similar to flats 1347 of the previously described embodiment, other embodiments may comprise such flats as well as a tool-engaging feature internal to a bore.

In the embodiment of FIGS. 45-49, tapered coronal portion 1435 comprises a longitudinal groove 1420 and a terminal portion 1437 with a pair of retention recesses 1410 transverse to a longitudinal axis 1419. In this embodiment, retention recesses 1410 are shown in interproximal positions and longitudinal groove 1420 is shown in a lingual position, but alternative embodiments may comprise recesses and grooves in alternate locations.

Terminal portion 1437 is generally equivalent to the terminal portions described in certain previous embodiments, such as terminal portion 137 of the embodiment shown in FIGS. 1-4 Terminal portion 1437 comprises a non-frustoconical surface having a lingual arcuate surface 1438 and a facial arcuate surface 1439. As previously described, the configuration of terminal portion 1437 minimizes the amount of preparation work that needs to be performed before a prosthetic tooth is installed. In addition, the area of tapered coronal portion 1435 near margin shoulder 1450 flares outwardly to provide a base or ledge for a prosthetic tooth to seat against after installation onto implant 1400

Figure 46:
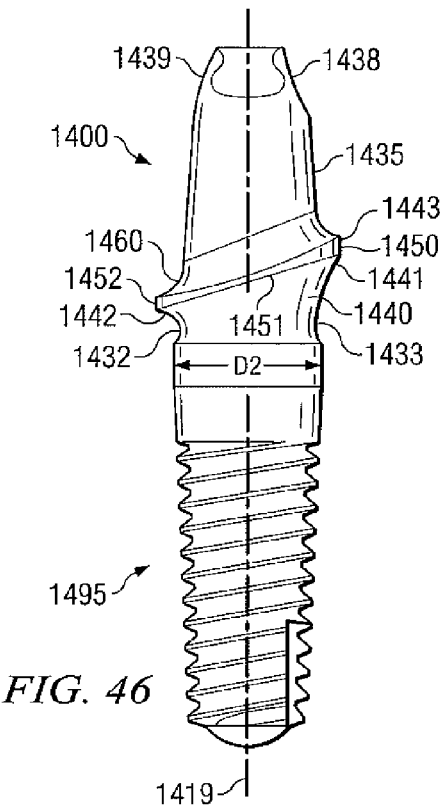
FIG. 46 is an interproximal view of the embodiment of FIG. 45.
Figure 47:
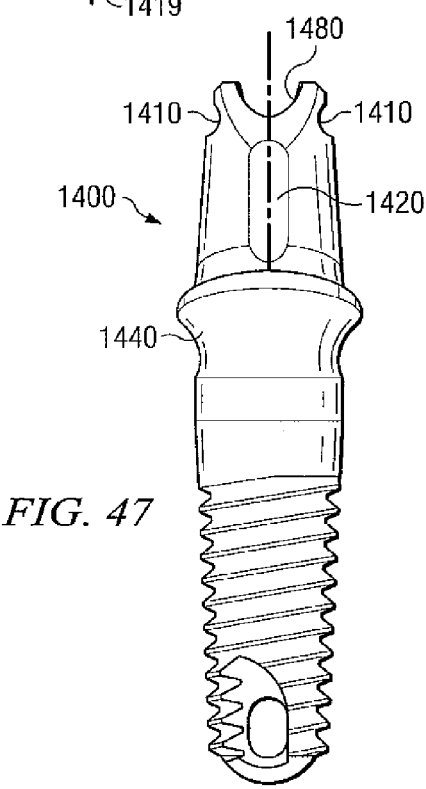
FIG. 47 is a lingual view of the embodiment of FIG. 45.
Figure 48:
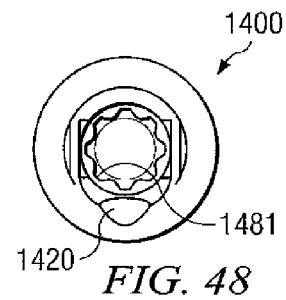
FIG. 48 is a coronal view of the embodiment of FIG. 45.
Figure 49:
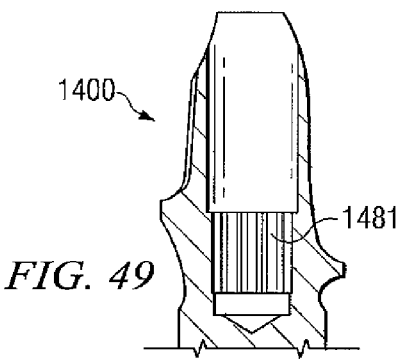
FIG. 49 is a partial section view of the embodiment of FIG. 45.
Figure 50:
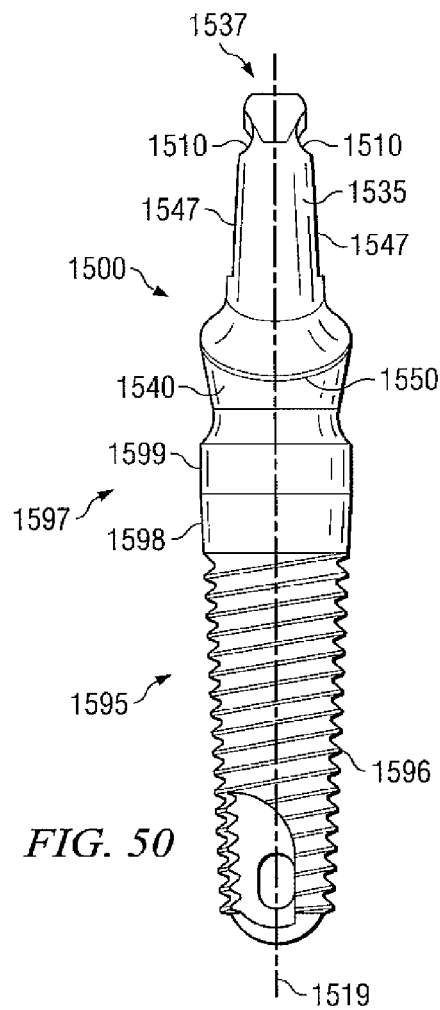
FIG. 50 is a facial view of one embodiment of a component of the system.

As shown in FIG. 46, margin shoulder 1450 is disposed between tapered coronal portion 1435 and emergence profile portion 1440. Margin shoulder 1450 comprises an arcuate transition zone 1460, which may comprise a radius of curvature that varies along its profile. Margin shoulder 1450 further comprises an interproximal aspect 1451 that continuously slopes such that a lingual side 1443 of margin shoulder 1450 is higher than a facial side 1452 of margin shoulder 1450. Interproximal aspect 1451 of margin shoulder 1450 continuously slopes such that there are no positive-to-negative or negative-to-positive changes in slope from lingual side 1443 to facial side 1452. Also shown in FIG. 46, a lingual aspect 1441 of emergence profile portion 1440 has a greater longitudinal length than a facial aspect 1442 of emergence profile portion 1440.

In addition, adjacent to body portion 1495, emergence profile portion 1440 comprises a facial concave surface 1432 and a lingual concave surface 1433. As previously described, concave surfaces 1432 and 1433 provide more room for soft tissue and bone growth, improving aesthetics and reducing the likelihood of infection. As shown in FIG. 46, concave surfaces 1432 and 1433 extend within an outer envelope diameter D2 of upper threaded body portion 1495. Concave surfaces 1432 and 1433 may comprise various configurations other than that shown in FIGS. 45-49. For example, concave surfaces 1432 and 1433 may comprise either multiple or a single radius of curvature and may extend different depths into emergence profile portion 1440. In addition, the center of curvature for concave surface 1432 may be located either within outer envelope diameter D2 or outside of outer envelope diameter D2. In the embodiment of FIGS. 45-49, lingual concave surface 1433 has a greater radius of curvature than facial concave surface 1432, and facial concave surface 1432 extends farther into emergence profile portion 1440 than does lingual concave surface 1433.

As shown in the embodiment of FIGS. 45-49, body portion 1495 comprises a threaded portion 1496 and a non-threaded collar portion 1497 which, in turn, comprises a tapered section 1498 having a frustoconical surface and a cylindrical section 1499. In certain embodiments, threaded portion 1496 is tapered and comprises double-lead or triple-lead threads, and non-threaded collar portion 1497 comprises a roughened surface.

Another embodiment of a unibody implant is shown in FIGS. 50-53 as implant 1500. Similar to the embodiment of FIGS. 41-44, unibody implant 1500 includes an emergence profile portion 1540 disposed between body portion 1595 and a tapered coronal portion 1535. Unibody implant 1500 further comprises a margin shoulder 1550 between emergence profile portion 1540 and tapered coronal portion 1535.

In the embodiment shown, tapered coronal portion 1535 includes a pair of flats 1547, a longitudinal groove 1520 and a terminal portion 1537 with a pair of retention recesses 1510 transverse to a longitudinal axis 1519. In this embodiment, flats 1547 and retention recesses 1510 are shown in interproximal positions and longitudinal groove 1520 is shown in a lingual position, but alternative embodiments may comprise flats, recesses or grooves in alternate locations. Flats 1547 may be used to rotate implant 1500 to assist in threadably engaging implant 1500 with a patient's bone during installation of implant 1500.

Terminal portion 1537 is generally equivalent to the terminal portions described in certain previous embodiments, such as terminal portion 137 of the embodiment shown in FIGS. 1-4. Terminal portion 1537 comprises a non-frustoconical outer surface having a lingual arcuate surface 1538, a facial arcuate surface 1539 and retention recess 1510. As previously described, the configuration of terminal portion 1537 minimizes the amount of preparation work that needs to be performed before a prosthetic tooth is installed. In addition, the area of tapered coronal portion 1535 near margin shoulder 1550 flares outwardly to provide a base or ledge for a prosthetic tooth to seat against after installation onto implant 1500.

Figure 51:
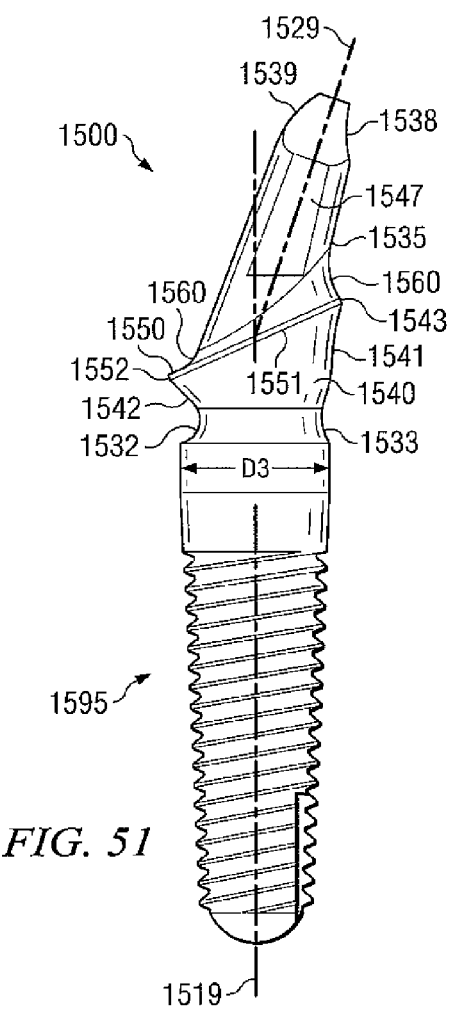
FIG. 51 is an interproximal view of the embodiment of FIG. 50.
Figure 52:
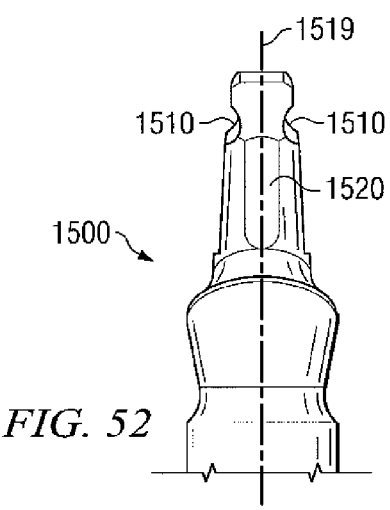
FIG. 52 is a partial lingual view of the embodiment of FIG. 50.
Figure 53:
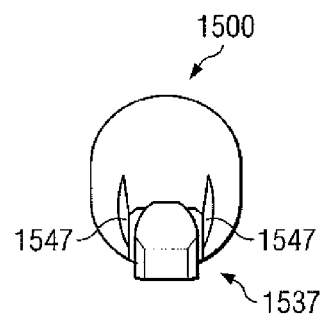
FIG. 53 is a coronal view of the embodiment of FIG. 50.

As shown in FIG. 51, margin shoulder 1550 is disposed between tapered coronal portion 1535 and emergence profile portion 1540. Margin shoulder 1550 comprises an arcuate transition zone 1560, which may include a radius of curvature that varies along its profile. Margin shoulder 1550 further comprises an interproximal aspect 1551 that continuously slopes such that a lingual side 1543 of margin shoulder 1550 is higher than a facial side 1552 of margin shoulder 1550, the continuous slope having no positive-to-negative or negative-to-positive changes. Also shown in FIG. 51, a lingual aspect 1541 of emergence profile portion 1540 has a greater longitudinal length than a facial aspect 1542 of emergence profile portion 1540.

In addition, adjacent to body portion 1595, emergence profile portion 1540 comprises a facial concave surface 1532 and a lingual concave surface 1533. As shown in FIG. 51, concave surfaces 1532 and 1533 extend within an outer envelope diameter D3 of upper threaded body portion 1595. Concave surfaces 1532 and 1533 may comprise various configurations other than that shown in FIGS. 50-53. For example, concave surfaces 1532 and 1533 may comprise either multiple or a single radius of curvature and may extend different depths into emergence profile portion 1540. In addition, the center of curvature for concave surface 1532 may be located either within outer envelope diameter D3 or outside of outer envelope diameter D3. In the embodiment of FIGS. 50-53, lingual concave surface 1533 has a greater radius of curvature than facial concave surface 1532, and facial concave surface 1532 extends farther into emergence profile portion 1540 than does lingual concave surface 1533.

As shown in the embodiment of FIGS. 50-53, body portion 1595 comprises a threaded portion 1596 and a non-threaded collar portion 1597. Collar portion 1597 comprises a tapered section 1598 and a cylindrical section 1599. In certain embodiments, threaded portion 1596 is tapered and comprises double-lead or triple-lead threads, and non-threaded collar portion 1597 comprises a roughened surface.

As shown in FIG. 51, unlike the embodiment of FIGS. 41-44, tapered coronal portion 1535 comprises a center axis 1529 that is set at an angle from a longitudinal axis 1519 that passes through the center of body portion 1595. In this embodiment, center axis 1529 is set at an angle of 17 degrees from longitudinal axis 1519. In other embodiments, center axis 1529 is set an angle other than 17 degrees. Unibody implant 1500 may fairly be described and referred to herein as an "angled one piece implant" or as an "angled unibody implant" given that post portion 1535 is angled relative to body portion 1595 and axis 1519, and that post portion 1535 is integral with body portion 1595.

Referring now to FIGS. 54-58, another embodiment of an angled unibody implant is shown as implant 1600. Similar to the embodiment of FIGS. 45-49, this embodiment comprises an emergence profile portion 1640 disposed between body portion 1695 and a tapered coronal portion 1635. Unibody implant 1600 further comprises a margin shoulder 1650 between emergence profile portion 1640 and tapered coronal portion 1635.

Unibody implant 1600 comprises the same general configuration as implant 1500, but tapered coronal portion 1635 also incorporates an internal bore 1680 with a tool-engaging feature 1681 (see FIGS. 57 and 58) that may be used to rotate implant 1600 and assist in threadably engaging implant 1600 into a patient's jaw bone. In the embodiment shown, tool-engaging feature 1681 is a polygonal end of internal bore 1680. While the embodiment of FIGS. 54-58 is shown not to include outer flats similar to flats 1547 of the previously described embodiment, other embodiments may comprise both outer flats and an internal tool-engaging feature.

In the embodiment of FIGS. 54-58, tapered coronal portion 1635 comprises a longitudinal groove 1620 and a terminal portion 1637 with a pair of retention recesses 1610 transverse to a longitudinal axis 1619. In this embodiment, retention recesses 1610 are shown in an interproximal position and longitudinal groove 1620 is shown in a lingual position, but alternative embodiments may comprise recesses and grooves in alternate locations.

Terminal portion 1637 is generally equivalent to the terminal portions described in certain previous embodiments, such as terminal portion 137 of the embodiment shown in FIGS. 1-4. Terminal portion 1637 comprises a non-frustoconical shape having a lingual arcuate surface 1638 and a facial arcuate surface 1639. As previously described, the configuration of terminal portion 1637 minimizes the amount of preparation work that needs to be performed before a prosthetic tooth is installed. In addition, the area of tapered coronal portion 1635 near margin shoulder 1650 flares outwardly to provide a base or ledge for a prosthetic tooth to seat against after installation onto implant 1600.

As shown in FIG. 55, margin shoulder 1650 is disposed between tapered coronal portion 1635 and emergence profile portion 1640. Margin shoulder 1650 comprises an arcuate transition zone 1660, which may comprise a radius of curvature which varies along its profile. Margin shoulder 1650 further comprises an interproximal aspect 1651 that continuously slopes such that a lingual side 1643 of margin shoulder 1650 is higher than a facial side 1652 of margin shoulder 1650. Also shown in FIG. 54, a lingual aspect 1641 of emergence profile portion 1640 has a greater longitudinal length than a facial aspect 1642 of emergence profile portion 1640.

In addition, adjacent to body portion 1695, emergence profile portion 1640 comprises a facial concave surface 1632 and a lingual concave surface 1633. As previously described, concave surfaces 1632 and 1633 provide more room for soft tissue and bone growth, improving aesthetics and reducing the likelihood of infection. As shown in FIG. 54, concave surfaces 1632 and 1633 extend within an outer envelope diameter D4 of upper threaded body portion 1695. Concave surfaces 1632 and 1633 may comprise various configurations other than that shown in FIGS. 54-58. For example, concave surfaces 1632 and 1633 may comprise either multiple or a single radius of curvature and may extend different depths into emergence profile portion 1640. In addition, the center of curvature for concave surface 1632 may be located either within outer envelope diameter D4 or outside of outer envelope diameter D4. In the embodiment of FIGS. 54-58, lingual concave surface 1633 has a greater radius of curvature than facial concave surface 1632 and extends farther into emergence profile portion 1640 than does lingual concave surface 1633.

As shown in the embodiment of FIGS. 54-58, body portion 1695 comprises a threaded portion 1696 and a non-threaded collar portion 1697. Collar portion 1697 comprises a tapered section 1698 and a cylindrical section 1699. In certain embodiments, threaded portion 1696 is tapered and comprises double-lead or triple-lead threads, and non-threaded collar portion 1697 comprises a roughened surface As shown in FIG. 55, unlike the embodiment of FIGS. 45-49, tapered coronal portion 1635 comprises a center axis 1629 that is set at an angle from a longitudinal axis 1619 that passes through the center of body portion 1695. In this embodiment, center axis 1629 is set at an angle of 17 degrees from longitudinal axis 1619. In other embodiments, center axis 1629 is set an angle other than 17 degrees. As shown in FIG. 58, bore 1680 is parallel with longitudinal axis 1619.

Another embodiment shown in FIGS. 59-60 comprises threads with different heights. This embodiment comprises a unibody implant 1700 with a threaded portion 1795 having an apical end 1796, an unthreaded cylindrical portion 1730, an emergence profile portion 1740, a margin 1722 and a tapered coronal or post portion 1735. In this embodiment, tapered coronal portion 1735 may comprise one of the various configurations described in other embodiments. The embodiment of FIGS. 59-60 comprises a shoulder 1731 (between cylindrical portion 1730 and emergence profile portion 1740) that serves as a reference line for the location of the thread portions with different heights.

In the embodiment shown, threaded portion 1795 comprises a first threaded section 1797 and a second threaded section 1798. First threaded section 1797 comprises threads with a thread height of slightly greater than 0.2 mm, while second threaded section 1798 comprises threads with a thread height that is much greater than 0.2 nm. In the embodiment shown, the axial distance from shoulder 1731 to the beginning of first threaded section 1797 (the end of first threaded section 1797 that is farthest from apical end 1796) is at least four percent of the distance from shoulder 1731 to apical end 1796. In other words, cylindrical portion 1730 (which does not have threads) is at least four percent of the axial length between shoulder 1731 and 1796. In other embodiments, cylindrical portion 1730 may comprise a greater percentage of the axial length between shoulder 1731 and apical end 1796.

The first and second threaded sections 1797 and 1798 may be single or multiple lead threads. Further, the first and second threaded sections may have a different number of thread leads. However, the first and second sections must be matched so that both threaded sections displace the implant vertically at the same rate as the implant is rotated.

Figure 61:
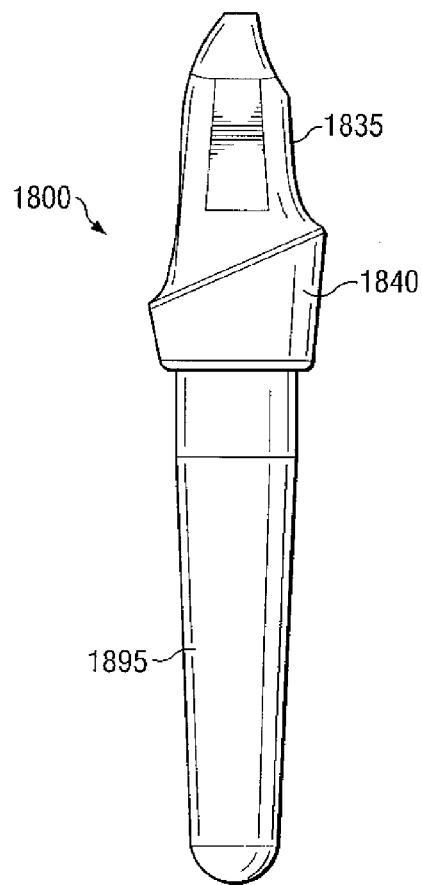
FIG. 61 is interproximal view of a component of the system.
Figure 62:
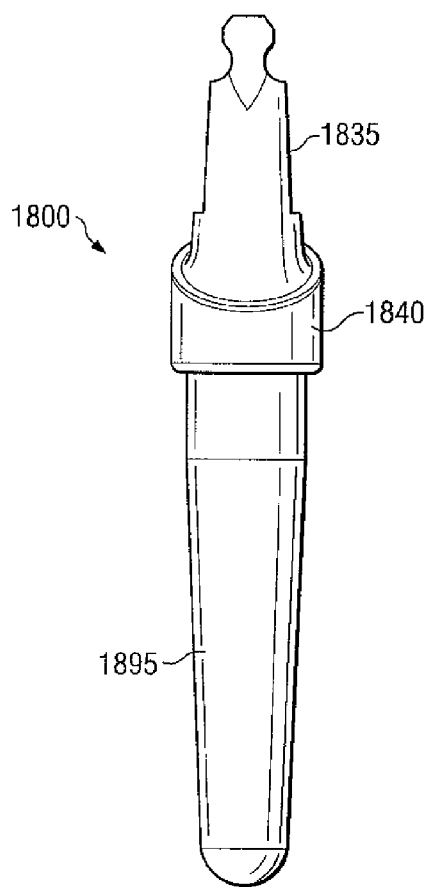
FIG. 62 is a facial view of the component of FIG. 61.

Another component of the dental system is shown in FIGS. 61 and 62. Implant 1800 is a fitting implant that can be used to assist a restorative dentist or surgeon in determining several things, including whether a unibody or two-stage (subgingival implant and separate abutment) implant should be used, or whether a straight or an angled abutment should be selected for permanent restoration It is important to determine if the direction suggested by the initial osteotomy will allow for the alignment of the integral restorative portion of the one-piece implant to satisfy the clinical parameters needed for a successful final restoration. These parameters include, but are not limited to, labial margin placement, inter-occlusal clearance, angulation (whether alone or in conjunction with other implants being placed), and room for final restorative material such as ceramics. Further, it is important to determine if an angulated one-piece implant (if such an implant is necessary) will be able to clear the adjacent teeth as it rotates in place upon final seating. The final decision for the use of a one-piece implant is generally not related to any of the components, including the implant, but rather to the surgeon's clinical impression of bone quality and potential for achieving adequate primary stability. The uniqueness of this protocol, utilizing the fitting implant at such an early and non-committed stage of the surgical process, allows for an increased level of surgical flexibility. The surgeon can either make changes to the direction of the osteotomy in order to better align the integral restorative portion on the one-piece or decide to go with a two-piece protocol, which allows for greater choices in restorative options without any significant addition to die surgical armamentarium.

Implant 1800 comprises a tapered coronal portion 1835 and emergence profile portion 1840 that are equivalent, or substantially similar, to any of the configurations in the previously-described embodiments. Implant 1800 comprises a tapered non-threaded body portion 1895 so that implant 1800 can be easily inserted and removed from the bore formed at the implant site in the patient's jaw to determine the size, shape and type of the desired permanent implant. Although implant 1800 shown in FIGS. 61 and 62 comprises a tapered coronal portion 1835 that is not angled with respect to non-threaded body portion 1895, other embodiments may comprise a coronal portion that is angled relative to non-threaded body portion 1895 Implant 1800 may be comprised of a material, such as plastic, that is less expensive than titanium or other material typically used for permanent implants.

Figure 63:
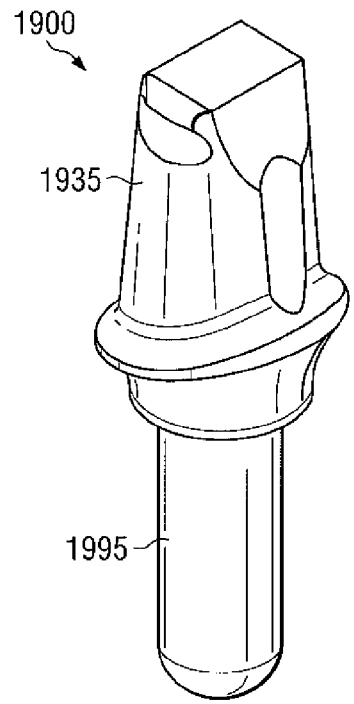
FIG. 63 is a perspective view of one embodiment of a component of the system.
Figure 63A:
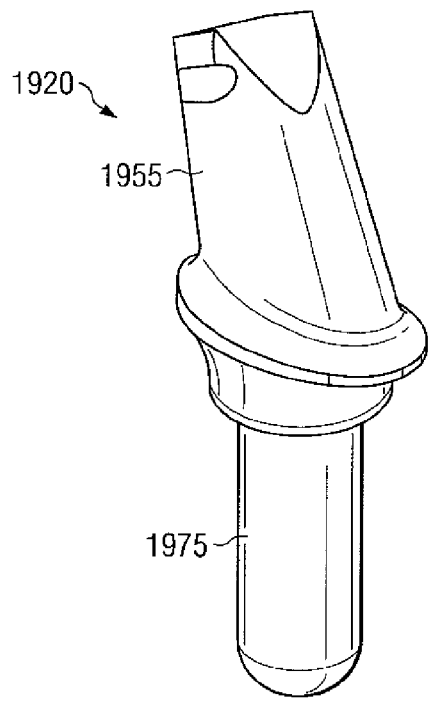
FIG. 63A is a perspective view of an alternative embodiment of the component of FIG. 63.

Another embodiment of a fitting implant is shown in FIG. 63 as implant 1900. This embodiment comprises the same general configuration as the embodiment of FIGS. 61 and 62, except implant 1900 has a body portion 1995 that is generally cylindrical rather than tapered. In the embodiment of FIG. 63, tapered coronal portion 1935 is not angled with respect to body portion 1995. The embodiment shown in FIG. 63A is generally equivalent to the embodiment of FIG. 63, with the exception that implant 1920 has a tapered coronal portion 1955 that is angled from non-threaded cylindrical portion 1975.

Another embodiment of an implant is shown in FIGS. 64 and 65 as implant 2000. Implant 2000 is an analog implant that is used to assist in making a model of the patient's mouth. Implant 2000 comprises a tapered coronal portion 2035, emergence profile portion 2040 and a body portion 2095. Tapered coronal portion 2035 and emergence profile portion 2040 are equivalent, or substantially similar, to any of the configurations in the previously-described embodiments. Body portion 2095 further comprises markings 2096 that identify the size and configuration of the implant, and retention recess 2075 that allow implant 2000 to be retained in the modeling material used to model the patient's mouth. As known by one skilled in the art, tapered coronal portion 2035 is inserted into an impression cap (not shown) after an impression is made of a patient's mouth. A stone model of the patient's mouth is then made from the impression mold and analog implant 2000 is retained in the model by retention recess 2075.

Figure 66:
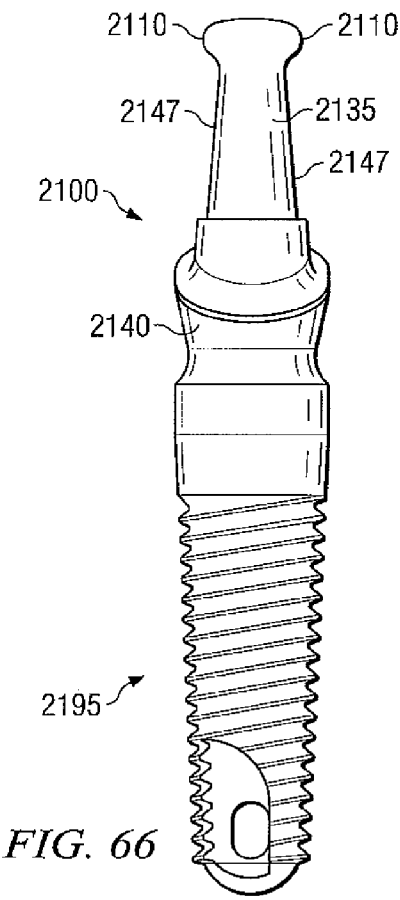
FIG. 66 is a facial view of an alternative embodiment of a system component.

Another embodiment of an implant is shown in FIG. 66 as implant 2100. Implant 2100 comprises a body portion 2195, an emergence profile portion 2140, and a tapered coronal portion 2135 with a pair of flats 2147. Unlike previously described embodiments, the embodiment of FIG. 66 comprises a pair of retention protrusions 2110 rather than retention recesses. Retention protrusions 2110 are configured to engage correspondingly sized and shaped grooves in an impression coping (not shown) or other attachment to implant 2100.

Figure 67:
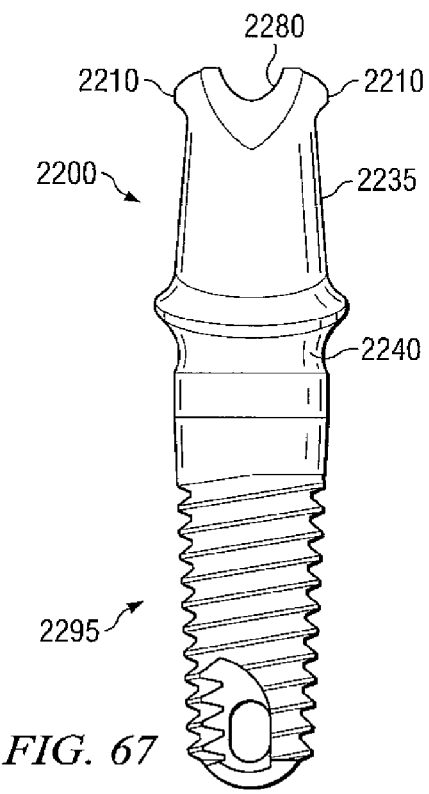
FIG. 67 is a facial view of an alternative embodiment of a system component.

Another embodiment of an implant is shown in FIG. 67 as implant 2200. Implant 2200 comprises a body portion 2295, an emergence profile portion 2240, and a tapered coronal portion 2235 with a bore 2280 and a tool engaging feature (not shown) similar to that shown in FIGS. 57 and 58 of a previous embodiment. Unlike previously described embodiments, the embodiment of FIG. 67 comprises a pair of retention protrusions 2210 rather than retention recesses Retention protrusions 2210 are configured to engage correspondingly sized and shaped grooves in an impression coping (not shown) or other attachment to implant 2200.

Figure 62A:
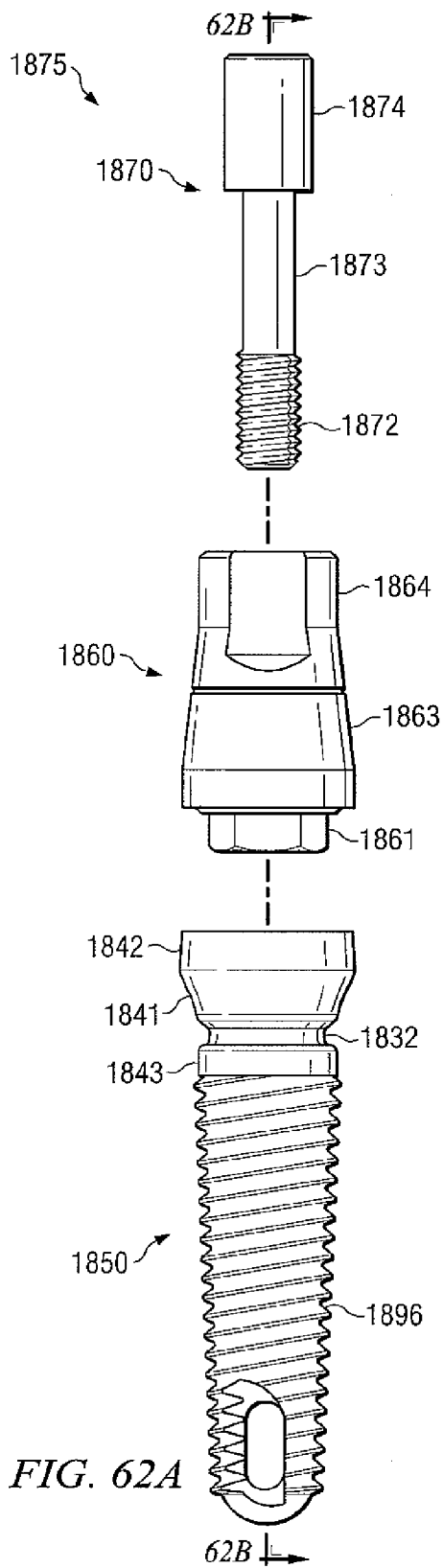
FIG. 62A is an exploded facial view of an alternative embodiment of the system.
Figure 62B:
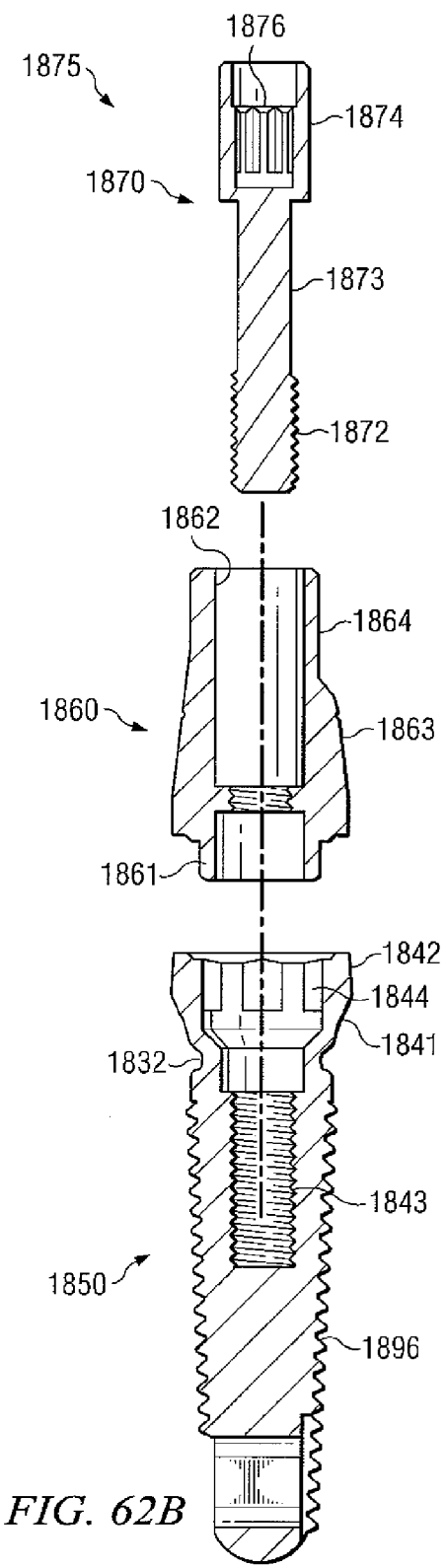
FIG. 62B is a section view of the embodiment of FIG. 62A.

As shown in FIGS. 62A through 62E, one embodiment of a two-stage implant system 1875 is shown to comprise an implant 1850, an abutment 1860 and a connection member 1870. Referring initially to FIGS. 62A and 62B, an exploded facial view of system 1875 is shown as well as a section view taken along line 62B in FIG. 62A. In this embodiment, emergence profile section 1841 is integral to implant 1850 rather than the abutment 1870. Implant 1850 includes a threaded portion 1896 and an emergence profile section 1841 with a concave portion 1832, which is similar to concave portion 330 shown in FIGS. 20 and 21. Implant 1850 also comprises a non-threaded cylindrical portion 1843 between threaded portion 1896 and emergence profile portion 1841. Implant 1850 also includes a tapered portion 1842 at the coronal end of the implant. As shown in the section view of FIG. 62B, implant 1850 comprises a threaded internal bore 1843 and a polygonal recess 1844 at its coronal end.

Abutment 1860 includes a central bore 1862 and is configured to engage implant 1850 via a polygonal base portion 1861. Abutment 1860 also comprises a flared body portion 1863 and an upper post portion 1864. Connection member 1870 is configured to connect abutment 1860 to implant 1850. Connection member 1870 includes a threaded portion 1872, a non-threaded shank 1873 and a head 1874 with an internal socket 1876.

Figure 62C:
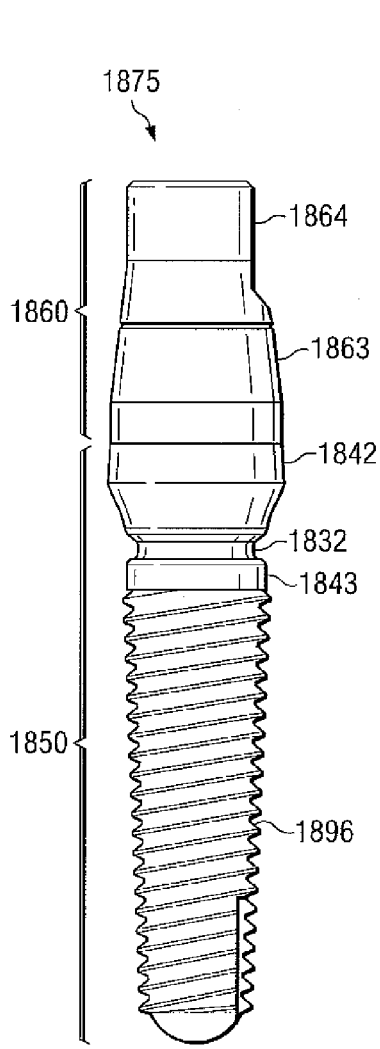
FIG. 62C is an interproximal view of the assembled embodiment of FIG. 62A.
Figure 62D:
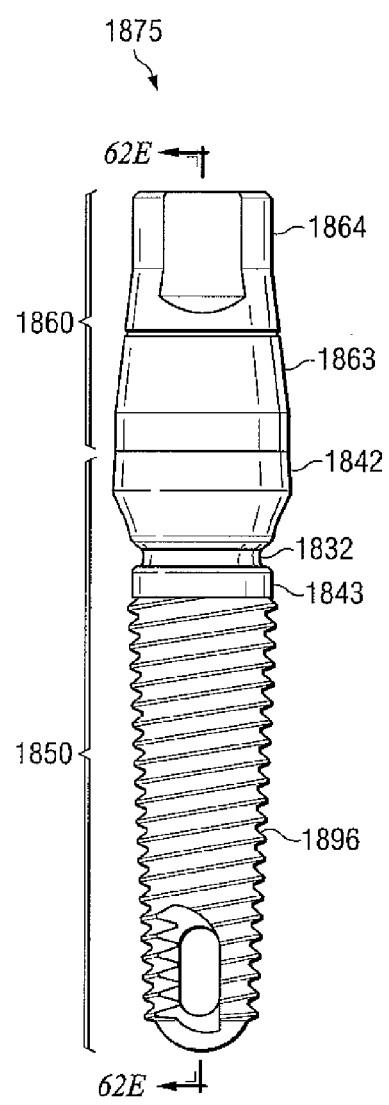
FIG. 62D is a facial view of the embodiment of FIG. 62C.
Figure 62E:
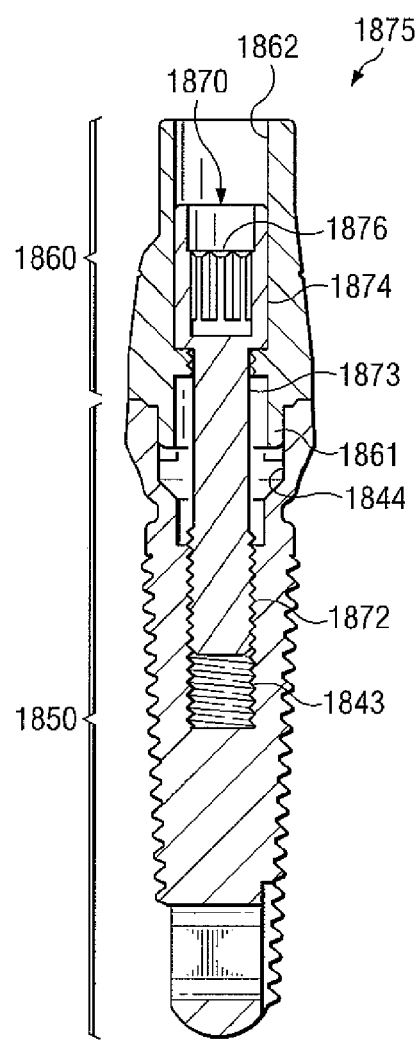
FIG. 62E is an interproximal section view of the embodiment of FIG. 62C.

Abutment 1860, may be connected to implant 1850 as shown in FIGS. 62C through 62E. FIG. 62C depicts an interproximal view of implant system 1875, while FIG. 62D depicts a facial view of implant system 1875. A section taken along line 62E in FIG. 62D is shown in FIG. 62E. As shown in FIG. 62E, polygonal base portion 1861 of abutment 1860 engages polygonal recess 1844 at its coronal end. Connection member 1870 can then be inserted through bore 1862 of abutment 1860 so that threaded portion 1872 engages threaded internal bore 1843. A driving tool (not shown) can then be used to engage internal socket 1876 and rotate connection member 1870 so that threaded portion 1872 is adequately engaged with threaded internal bore 1843 to securely connect abutment 1860 to implant 1850.

Figure 68:
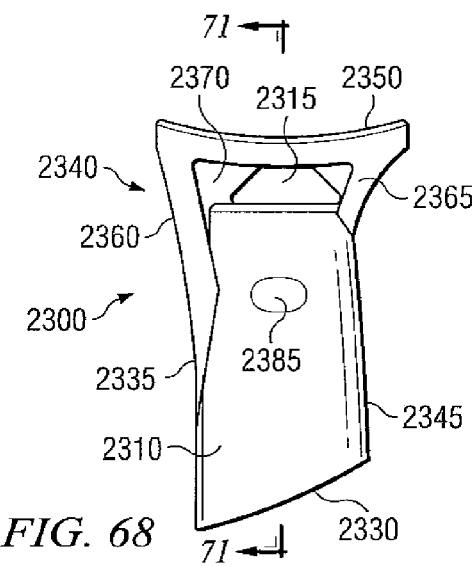
FIG. 68 is an interproximal view of one embodiment of a component of the system.
Figure 69:
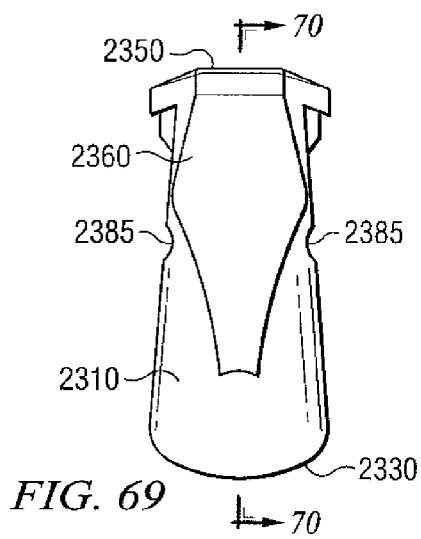
FIG. 69 is a facial view of the embodiment of FIG. 68.
Figure 70:
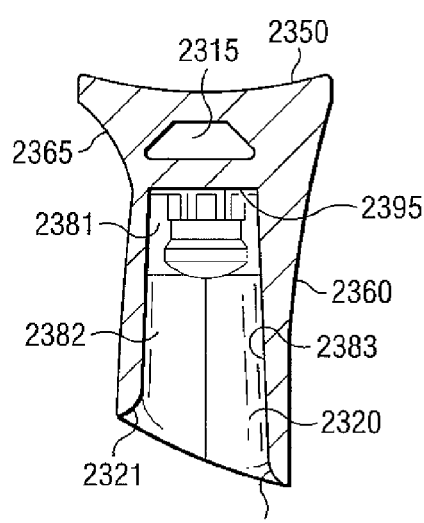
FIG. 70 is an interproximal section view of the embodiment of FIG. 68.
Figure 73:
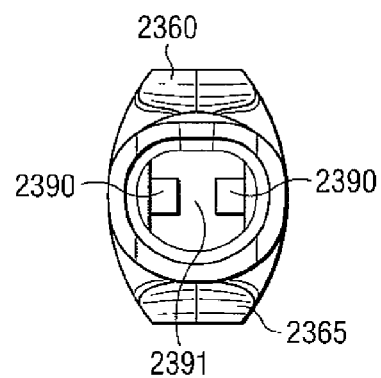
FIG. 73 is an apical view of the embodiment of FIG. 68.
Figure 71:
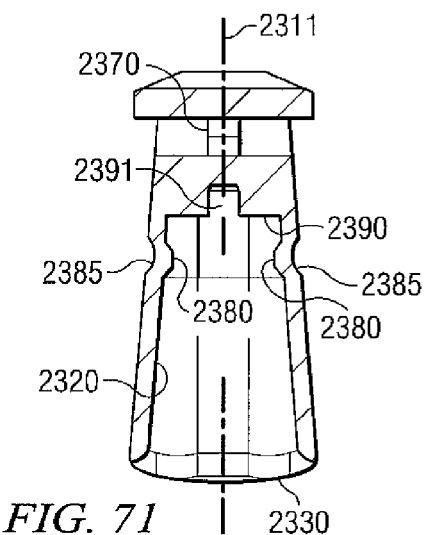
FIG. 71 is a lingual section view of the embodiment of FIG. 68.
Figure 72:
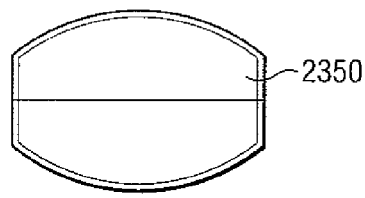
FIG. 72 is a coronal view of the embodiment of FIG. 68.

Referring now to FIGS. 68-73, an impression cap or coping 2300 is shown that may be used in conjunction with the previously described implants or abutments that are generally straight (i.e., have a tapered coronal portion that is parallel with the axis of the threaded portion or separate implant). The use of impression copings generally is well known in the art and involves seating the coping on an abutment or the coronal portion of an implant before taking an impression of the implant site in the patient's mouth. FIGS. 68 and 69 show impression coping 2300 in the interproximal and facial views, respectively, while FIGS. 70 and 71 are section views of FIGS. 68 and 69. FIGS. 72 and 73 represent the top (or coronal) view and bottom (or apical) view, respectively.

As shown in the embodiment of FIGS. 68-73, impression coping 2300 comprises a body portion 2310 with a longitudinal axis 2311 extending from an apical end 2330 to a coronal end 2340. Impression coping 2300 further comprises a facial aspect 2335, a lingual aspect 2345, and an internal bore or chamber 2320 extending from apical end 2330. Chamber 2320 has side walls 2383 which are non-frustoconical and an end wall 2395. Apical end 2330 comprises an arcuate edge 2321 (shown in FIG. 70) configured to engage or seat on an arcuate transition zone of a margin shoulder of an implant or abutment (not shown).

As discussed more fully below, coronal end 2340 comprises a number of ribs or flange portions that provide resistance to an impression material (not shown) used to make an impression of a patient's mouth. A first flange portion 2350 extends across coronal end 2340 and is generally parallel to a first plane that is perpendicular to longitudinal axis 2311. A second flange portion 2360 is generally parallel to a second plane that extends along facial aspect 2335 of body portion 2310, while a third flange portion 2370 extends between first flange portion 2350 and second flange portion 2360. Third flange portion 2370 is generally parallel to a third plane that is perpendicular to both the first plane and the second plane. A fourth flange portion 2365 extends along the lingual side of impression coping 2300 from first flange 2350 to body portion 2310.

In the embodiment shown, flange portions 2350, 2360, 2365 and 2370 therefore will provide resistance to movement between the impression coping and the impression material in three different lateral and rotational directions when an impression is made of the patient's mouth. For example, first flange portion 2350 will resist movement in a direction parallel to longitudinal axis 2311 and second and fourth flange portions 2360 and 2365 will resist movement in the facial/lingual lateral directions, i e., to the left or right in the view of FIG. 68. In addition, third flange portion 2370 will resist movement in the interproximal lateral direction, i.e., to the left or right in the view of FIG. 71. The flange portions will also provide resistance to rotational movement of impression coping 2300 relative to impression material. Using longitudinal axis 2311 as a reference, third flange 2370 will provide resistance to a rolling and a pitching movement of impression coping 2300. In addition, first flange portion 2350, second flange portion 2360 and fourth flange portion 2365 will provide resistance to a yawing movement of impression coping 2300. Reducing the movement between impression coping 2300 and the impression material will improve the accuracy of the mold created of the patient's mouth.

As shown in the section view of FIG. 71, impression coping 2300 comprises a pair of berm-like protrusions 2380 extending from internal chamber 2320. As explained more fully below, protrusions 2380 act as a retention mechanism and are configured to engage the retention recesses of the previously described implants and abutments. Also visible in FIGS. 68, 69 and 71 are a pair of indentations 2385 on the exterior of body portion 2310 Indentations 2385 reduce the cross-sectional thickness of body portion 2310 in the area proximal to protrusions 2380 and increase the ability of body portion 2310 to flex as protrusions 2380 engage retention recesses on an abutment or implant. Also shown in the embodiment of FIGS. 71 and 73, internal chamber 2320 comprises a pair of ribs or shoulders 2390 disposed at an axial position between protrusions 2380 and coronal end 2340. Shoulders 2390 are configured to act as a stop against the coronal end of an implant or abutment in the event a dental professional attempts to force coping 2300 too far onto an implant or abutment during installation. A recess or void 2391 such as a slot or bore is formed between shoulders 2390, further increasing the flexibility of body portion 2310.

The embodiment shown in FIGS. 68-73 also comprises an aperture 2315 extending through third flange portion 2370. A dental professional may pass a loop of dental floss (not shown) through aperture 2315 to prevent the impression coping from being dropped or lost during handling or placement of coping 2300 on a dental implant or abutment. Although aperture 2315 is shown in third flange portion 2370 in this embodiment, other embodiments may comprise an aperture in other portions of the impression coping. The aperture 2315 may be angular as shown, round, or other shapes.

The embodiment shown in FIGS. 68-73 is suited for use with an anatomical abutment or implant. For example, as shown in FIG. 68, facial aspect 2335 extends farther from coronal end 2340 than does lingual aspect 2345 In this manner, apical end 2330 slopes downward from lingual aspect 2345 to facial aspect 2335 to match the contour of the sloping margin shoulder in the previously described implants and abutments (e.g. interproximal aspect 151 of margin shoulder 150 shown in FIGS. 1 and 2). In addition, impression coping 2300 comprises internal bore or chamber 2320 having inner walls that are non-frustoconical and configured to generally correspond to the shape of an abutment or implant that has an anatomical shape. In certain embodiments, internal chamber 2320 is divided into two sections, a substantially cylindrical upper section 2381 and a non-frustoconical lower section 2382, as seen in FIG. 70. Protrusions 2380 are preferably located on the substantially cylindrical upper section 2381.

Figure 74:
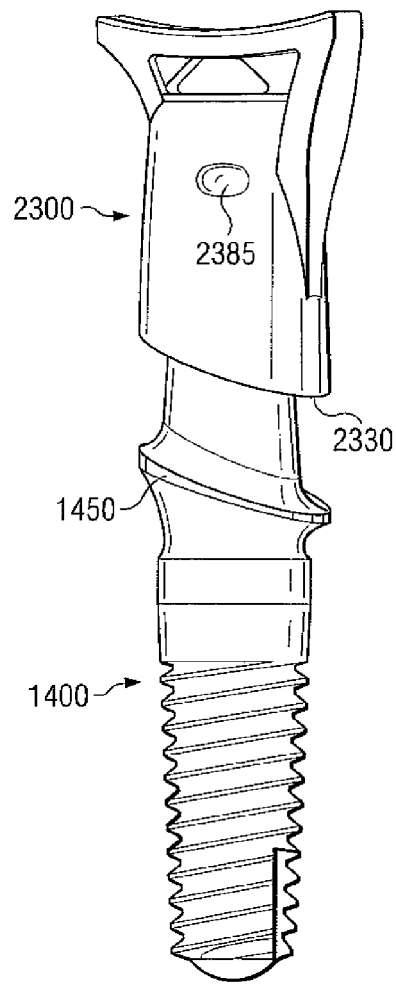
FIG. 74 is a partially exploded, interproximal assembly view of the embodiments of FIG. 68 and FIG. 45.
Figure 75:
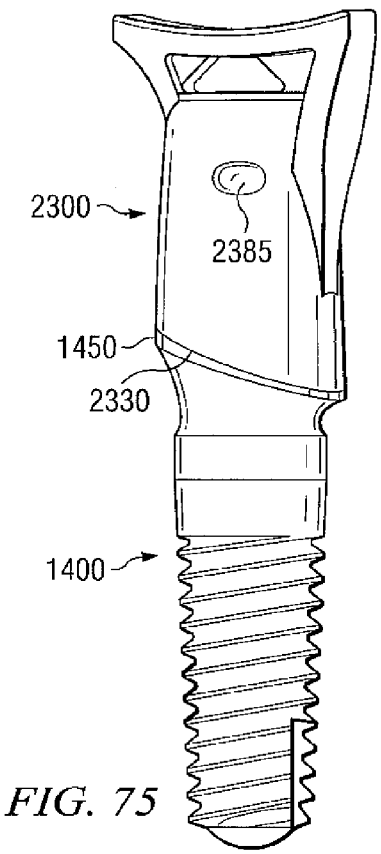
FIG. 75 is an assembly view of the embodiment of FIG. 74.
Figure 76:
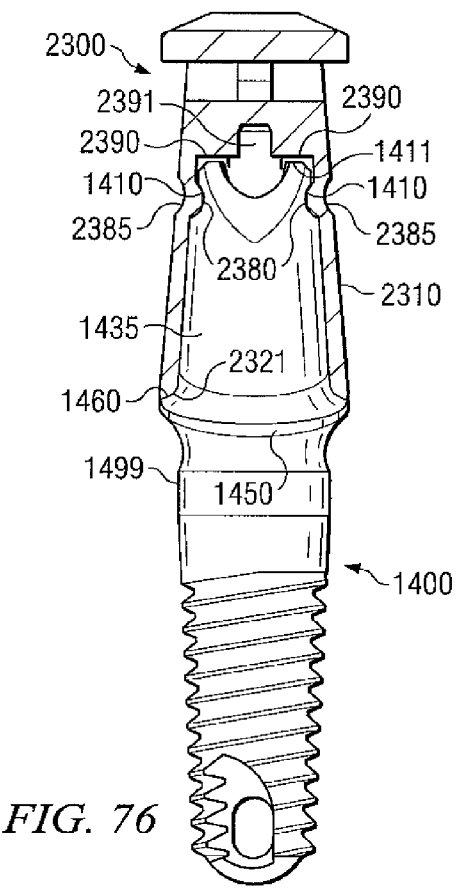
FIG. 76 is a partial section, facial assembly view of the embodiment of FIG. 75.

In certain embodiments, the impression coping may also be color-coded to indicate dimensional characteristics of the coping, such as the diameter of the internal chamber and whether the coping is configured for use with a straight or an angled dental implant or abutment. Still other embodiments may comprise a marking or indicator such as an etched, notched or recessed surface to indicate the dimensional characteristics of the coping FIGS. 74-76 illustrate the engagement of impression coping 2300 with implant 1400. Although not shown, impression coping 2300 may also be engaged with abutment 100 or other compatible dental components, such as fitting implant 1900 or analog implant 2000. FIG. 74 illustrates impression coping 2300 and implant 1400 in a partially-engaged configuration, while FIGS. 75 and 76 illustrate impression coping 2300 and implant 1400 in a fully-engaged position, where protrusions 2380 meet and engage retention recesses 1410.

As shown in FIG. 75, apical end 2330 is seated flush with margin shoulder 1450 upon full engagement of impression coping 2300 and implant 1400. FIG. 76 is a partial section view in which impression coping 2300 is shown in a section view and implant 1400 is shown from a facial perspective in a non-section view. As shown in FIG. 76, protrusions 2380 engage retention recess 1410 and retain impression coping 2300 on implant 1400. In the embodiment shown in FIG. 76, indentations 2385 reduce the cross-sectional thickness of implant 2300 in the area proximal to protrusions 2380 and thereby allow body portion 2310 to more easily flex and engage implant 1400.

Also visible in FIG. 76, shoulders 2390 are proximal to, but not contacting, a coronal end 1411 of tapered coronal portion 1435. As previously mentioned, shoulders 2390 are configured to prevent impression coping 2300 from being forced too far onto implant 1400. Also, void 2391 between shoulders 2390 provides further ability for body portion 2310 to flex upon the seating and unseating of coping 2300. Also visible in FIG. 76, interior chamber 2320 of impression coping 2300 is configured to match the general anatomic shape of tapered coronal portion 1435. Arcuate edge 2321 is also shown seated on arcuate transition zone 1460 of margin shoulder 1450.

Figure 77:
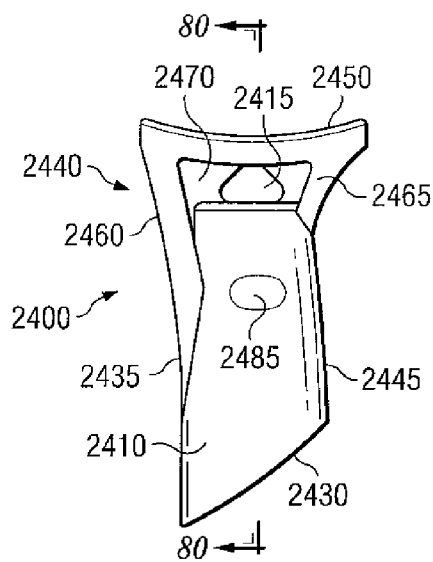
FIG. 77 is an interproximal view of one embodiment of a component of the system.
Figure 78:
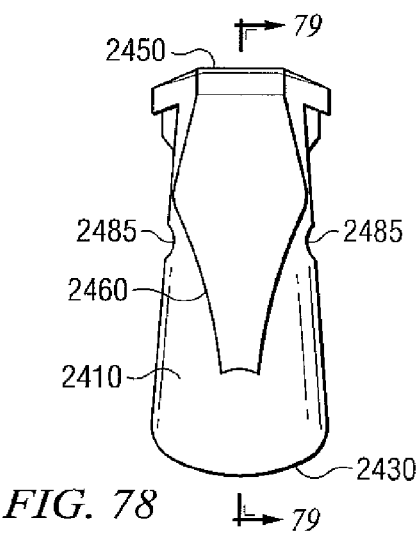
FIG. 78 is a facial view of the embodiment of FIG. 77.
Figure 79:
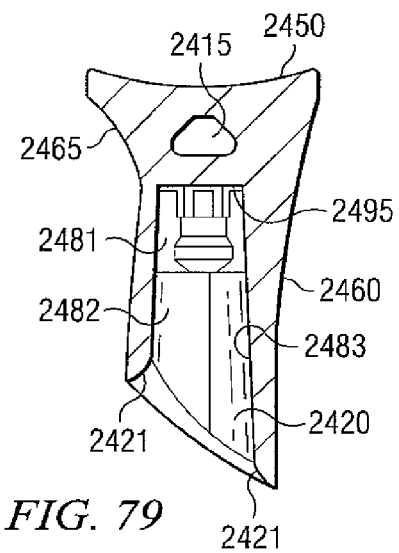
FIG. 79 is an interproximal section view of the embodiment of FIG. 77.
Figure 82:
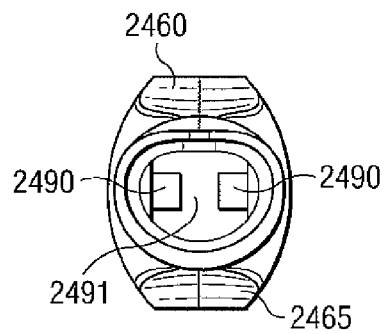
FIG. 82 is an apical view of the embodiment of FIG. 77.
Figure 80:
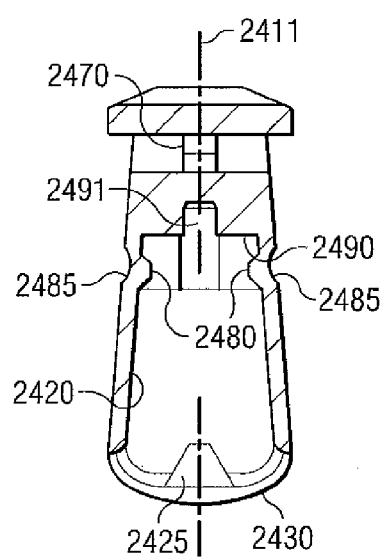
FIG. 80 is a lingual section view of the embodiment of FIG. 77.
Figure 81:
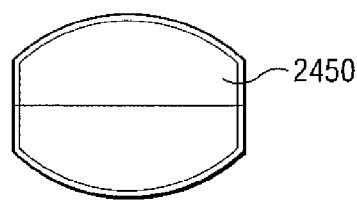
FIG. 81 is a coronal view of the embodiment of FIG. 77.

Referring now to FIGS. 77-82, an impression cap or coping 2400 is shown that can be used in conjunction with the previously described implants or abutments that are generally angled (i.e., the tapered coronal portion is angled from the threaded portion or separate implant). Although configured to fit angled abutments and implants, this embodiment is similar to the embodiment shown in FIGS. 68-73. FIGS. 77 and 78 show impression coping 2400 in the interproximal and facial views, respectively, while FIGS. 79 and 80 are section views of FIGS. 77 and 78. FIGS. 81 and 82 represent the top (or coronal) view and bottom (or apical) view, respectively.

As shown in the embodiment of FIGS. 77-82, impression coping 2400 comprises a body portion 2410 with a longitudinal axis 2411 extending from an apical end 2430 to a coronal end 2440. Impression coping 2400 further comprises a facial aspect 2435, a lingual aspect 2445 and an internal bore or chamber 2420 extending from apical end 2430. Chamber 2420 comprises a side wall 2483 with a substantially cylindrical upper section 2481 and a non-frustoconical lower section 2482 and an end wall 2495, as seen in FIG. 79. Apical end 2430 comprises an arcuate edge 2421 (shown in FIG. 79) configured to engage or seat on an arcuate transition zone of a margin shoulder of an implant or abutment (not shown). Similar to the embodiment of FIGS. 68-73, coronal end 2440 comprises a first flange 2450, a second flange 2460, a third flange 2470 and a fourth flange 2465.

As shown in the section view of FIG. 80, impression coping 2400 comprises a pair of protrusions 2480 extending inwardly from substantially cylindrical upper section 2481 of chamber 2420. In the embodiment shown, protrusions 2480 act as a retention mechanism and are configured to engage the retention recesses of the previously described implants and abutments. Also visible in FIGS. 77, 78 and 80 are a pair of indentations 2485 on the exterior of body portion 2410 that are similar to indentations 2385 of the previous embodiment. As shown in FIGS. 80 and 82, internal bore 2420 comprises a pair of ribs or shoulders 2490 that are equivalent to shoulders 2390 and a recess or void 2491 that is equivalent to void 2391 of the embodiment of FIGS. 68-73. The embodiment shown in FIGS. 77-82 also comprises an aperture 2415 that is similar to aperture 2315 of the previous embodiment. Also visible in the section view of FIG. 80 is an indicator 2425 on internal bore 2420 used to express that impression coping 2400 is intended to be used for an angled implant or abutment. In this embodiment, indicator 2425 is a recessed trapezoidal-shaped portion with angled sides.

The embodiment shown in FIGS. 77-82 is also suited for use with an anatomical abutment or implant. For example, as shown in FIG. 77, facial aspect 2435 extends farther from coronal end 2440 than does lingual aspect 2445. In this manner, apical end 2430 slopes downward from lingual aspect 2445 to facial aspect 2435 to match the contour of the sloping margin shoulder in the previously described implants and abutments (e.g., margin shoulder 650 shown in FIGS. 22 and 23). However, in the embodiment of FIGS. 77-82 the difference between facial aspect 2435 and lingual aspect 2445 is greater than the difference between facial aspect 2335 and lingual aspect 2345 shown in FIG. 68 of the previous embodiment. In order to accommodate an angled coronal portion of an implant or abutment, apical end 2430 of impression cap 2400 therefore slopes downward at a greater angle than apical end 2330. The other features of the embodiment of FIGS. 77-82 are generally equivalent to those found on the embodiment of FIGS. 68-73.

Figure 83:
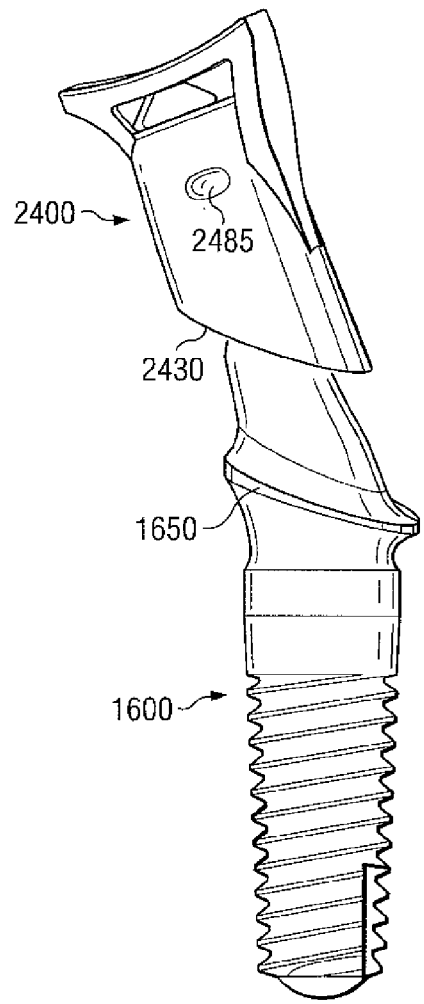
FIG. 83 is a partially exploded, interproximal assembly view of the embodiments of FIG. 77 and 54.
Figure 84:
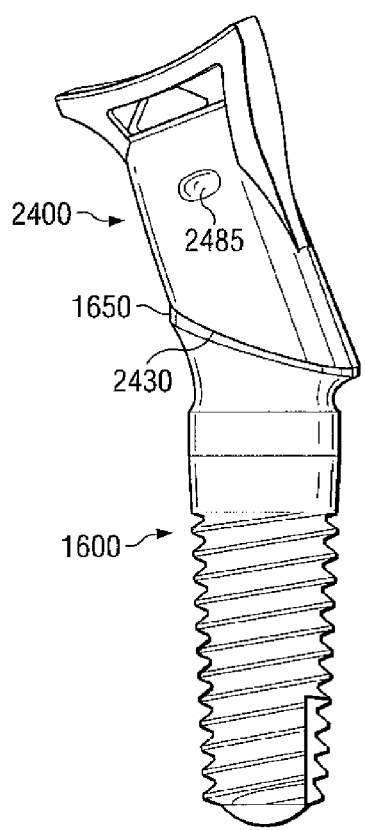
FIG. 84 is an assembly view of the embodiment of FIG. 83.
Figure 85:
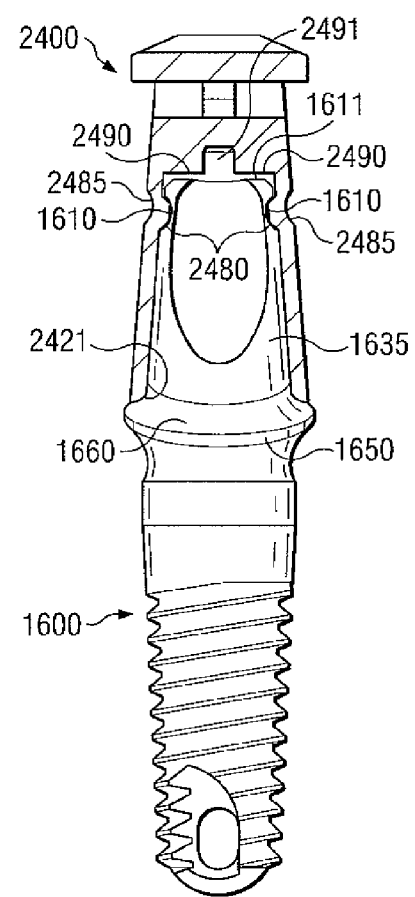
FIG. 85 is a partial section, facial assembly view of the embodiment of FIG. 83.

Similar to FIGS. 74-76, FIGS. 83-85 illustrate the engagement of impression coping 2400 with angled one piece implant 1600. Although not shown, impression coping 2400 may also be engaged with abutment 600 or other compatible abutments. FIG. 83 illustrates impression coping 2400 and implant 1600 in a partially-engaged configuration, while FIGS. 84 and 85 illustrate impression coping 2400 and implant 1600 in a fully-engaged position.

As shown in FIG. 84, apical end 2430 is seated flush with margin shoulder 1650 upon full engagement of impression coping 2400 and implant 1600. FIG. 85 is a partial section view in which implant 1600 is shown from a facial perspective in a non-section view and impression coping 2400 is shown in a section view, so that tapered coronal portion 1635 is visible after engagement with impression coping 2400. In the embodiment shown in FIG. 85, indentations 2485 reduce the cross-sectional thickness of implant 2400 in the area proximal to protrusions 2480 and thereby allow body portion 2410 to more easily flex and engage implant 1600.

As shown in FIG. 85, protrusions 2480 engage retention recesses 1610 and retain impression coping 2400 on implant 1600. Also visible in FIG. 85, shoulders 2490 are proximal to, but not contacting, a coronal end 1611 of tapered coronal portion 1635. As previously mentioned, shoulders 2490 are configured to prevent impression coping 2400 from being forced too far onto implant 1600. A void 2491 between shoulders 2490 provides further ability for body portion 2410 to flex upon the seating and unseating of coping 2400. Also visible in FIG. 85, interior chamber 2420 of impression coping 2400 is configured to match the general anatomic shape of tapered coronal portion 1635. Arcuate edge 2421 is also shown seated on arcuate transition zone 1660 of margin shoulder 1650.

While various preferred embodiments have been shown and described, modifications thereof can be made by one skilled in the art without departing from the spirit and teachings herein. The embodiments herein are exemplary only, and are not limiting. Many variations and modifications of the systems and components disclosed herein are possible and within the scope of this teaching. For example, the shape and orientation of the retention recesses and lingual groove may be different from that depicted. In addition, features from different embodiments described above can be combined to form other embodiments of the system. For example, other embodiments may comprise the tapered coronal portion of the embodiment of FIGS. 41-44 and the threaded sections of different heights found in the embodiment of FIGS. 59 and 60. In addition, the angled tapered coronal portion in each of the embodiments shown may be straight in other embodiments, and vice versa. Furthermore, the interproximal flats shown in the embodiment of FIGS. 7-9 may be included on any of the embodiments shown and the retention protrusions of FIGS. 66 and 67 may be used in addition to, or in place of, the retention recess on the other embodiments

What is claimed is:

1. A dental abutment having a longitudinal axis, a lingual aspect and a facial aspect, the abutment comprising:
    a base portion for engagement with a dental implant;
    a tapered coronal portion defining a coronal extremity spaced proximally from said base portion; the tapered coronal portion having an apical bottom;
    an emergence profile portion being disposed between said base portion and said tapered coronal portion, said emergence profile portion generally defining a longitudinal direction and comprising:
        at least a first concave surface,
        at least a first convex surface, and
        a chamfer having an apical edge forming a junction with the base portion, and a coronal edge disposed apically relative to the first concave surface and the first convex surface such that the first concave surface and the first convex surface of the emergence profile portion are both disposed coronally relative to the coronal edge of the chamfer, the chamfer forming a short ring so that the coronal edge is substantially closer to the apical edge than the first convex surface entirely around the abutment, and the chamfer being sloped to extend radially outward as the chamfer extends coronally from the apical edge to the coronal edge,
    wherein the combined longitudinal length of the first concave surface and the first convex surface forms a longer portion of the emergence profile portion than the longitudinal length of the chamfer; and
    a margin shoulder positioned between the emergence portion and the apical bottom of the tapered coronal portion, the margin shoulder having a lingual side and a facial side, the margin shoulder extending interproximally from the lingual side to the facial side such that the margin shoulder continuously slopes apically from the apical bottom of the tapered coronal portion, wherein the facial side of the margin shoulder is positioned closer to the base portion than is the lingual side of the margin shoulder; the margin shoulder further defining an arcuate transition zone positioned axially along the apical bottom of the tapered coronal portion, the transition zone formed by an increasing radius of the apical bottom of the tapered coronal portion in an apical direction, such that the apical bottom of the tapered coronal portion flares continuously radially outwardly to the radially outermost edge of the margin shoulder,
    wherein the first concave surface and the first convex surface of the emergence profile portion are both disposed apically relative to the margin shoulder.

2. The dental abutment of claim 1 wherein an upper portion of said first concave surface is contiguous with a lower portion of said first convex surface.

3. The dental abutment of claim 1 wherein each of said concave and said convex surfaces includes a radius of curvature, and at least one of said surfaces has a longitudinal length and said radius of curvature varies along said length.

4. The dental abutment of claim 1 wherein said longitudinal length of said emergence profile portion is greater in the lingual aspect than in the facial aspect.

5. The dental abutment of claim 1 wherein said concave surface further comprises a concave recess.

6. The dental abutment of claim 1 wherein said extremity of the tapered coronal portion comprises a coronal end portion having an exterior with at least one retention recess configured for longitudinally securing an impression coping to the coronal end portion.

7. The dental abutment of claim 6 wherein said retention recess is a groove, and is disposed on an interproximal aspect of said tapered coronal portion and elongate in a transverse direction relative to the longitudinal axis.

8. The dental abutment of claim 1 wherein said tapered coronal portion comprises a non-frustoconical upper portion.

9. The dental abutment of claim 8 wherein said upper portion comprises a pair of opposing arcuate surfaces wherein the center of curvature of both arcuate surfaces is on the same side of the arcuate surfaces.

10. The dental abutment of claim 1 wherein said emergence profile portion further comprises a second convex surface having a second radius of curvature less than a radius of curvature of said first convex surface.

11. The dental abutment of claim 1 further comprising a longitudinal groove disposed on a lingual aspect of said tapered coronal portion.

12. The dental abutment of claim 1 wherein said base portion comprises a polygonal outer surface.

13. The dental abutment of claim 1 further comprising an internal longitudinal bore having a shoulder and a threaded region.

14. The dental abutment of claim 1 further comprising at least one flat portion in an upper interproximal region of said emergence profile portion.

15. The dental abutment of claim 1 wherein said tapered coronal portion comprises a center axis set at an angle from the abutment longitudinal axis.

16. The dental abutment of claim 1 wherein said emergence profile portion further comprises a coating.

17. The dental abutment of claim 15 wherein a portion of said dental abutment comprises a roughened surface.

18. The dental abutment of claim 16 wherein said emergence profile portion further comprises a colorized surface.

19. The dental abutment of claim 18 wherein said emergence profile further comprises a nitride surface.

20. A set comprising a plurality of dental abutments, each abutment incorporating the dental abutment of claim 1, and wherein said emergence profile portion has a total longitudinal length that varies for each of said plurality of dental abutments.

21. The dental abutment of claim 1, further comprising a shoulder disposed between said emergence profile portion and said tapered coronal portion, said shoulder including an arcuate transition zone and sloping continuously apically from a lingual-most point to a facial-most point along the shoulder.

22. A dental abutment having a longitudinal axis, the abutment comprising:
  a base portion for engagement with a dental implant;
  a tapered coronal portion having a non-frustoconical upper portion, and defining a coronal extremity spaced proximally from said base portion; the tapered coronal portion having an apical bottom;
  an emergence profile portion disposed between said base portion and said tapered coronal portion, said emergence profile portion and said tapered coronal portion, said emergence profile portion general defining a longitudinal direction and comprising:
    at least a first concave surface;
    at least a first convex surface, and
    a chamfer having an apical edge and a coronal edge, wherein the first concave surface and the first convex surface of the emergence profile portion are both disposed coronally relative to the coronal edge of the chamfer, and wherein the chamfer forms a short ring so that the coronal edge is substantially closer to the apical edge than the first convex surface entirely around the abutment, and the chamfer is sloped to extend radially outward as the chamfer extends coronally from the apical edge to the coronal edge, and wherein the apical end extends radially outward from the base portion to the apical edge,
  wherein the combined longitudinal length of the first concave surface and the first convex surface forms a longer portion of the emergence profile portion than the longitudinal length of the chamfer; and
  a margin shoulder positioned between the emergence portion and the apical bottom of the tapered coronal portion, the margin shoulder having a lingual side and a facial side, the margin shoulder extending interproximally from the lingual side to the facial side such that the margin shoulder continuously slopes apically from the apical bottom of the tapered coronal portion, wherein the facial side of the margin shoulder is positioned closer to the base portion than is the lingual side of the margin shoulder; the margin shoulder further defining an arcuate transition zone positioned axially along the apical bottom of the tapered coronal portion, the transition zone formed by an increasing radius of the apical bottom of the tapered coronal portion in an apical direction, such that the apical bottom of the tapered coronal portion flares continuously radially outwardly to the radially outermost edge of the margin shoulder,
  wherein the first concave surface and the first convex surface of the emergence profile portion are both disposed apically relative to the margin shoulder.

23. The dental abutment of claim 22 wherein said non-frustoconical upper portion comprises a coronal end portion having an exterior with at least one retention recess configured for longitudinally securing an impression coping to the coronal end portion.

24. The dental abutment of claim 23 wherein said non-frustoconical upper portion comprises an outer circumference and said retention extends only partially around said outer circumference.

25. The dental abutment of claim 23 wherein said retention recess is disposed on an interproximal aspect of said tapered coronal portion, and is elongate in a transverse direction relative to the longitudinal axis.

26. The dental abutment of claim 22 wherein a portion of said shoulder comprises a segment of a cone.

27. The dental abutment of claim 22 wherein said non-frustoconical upper portion comprises a pair of opposing arcuate surfaces.

28. The dental abutment of claim 22 further comprising a longitudinal groove disposed on a lingual aspect of said tapered coronal portion between said shoulder and said non-frustoconical upper portion.

29. The dental abutment of claim 22 further comprising a longitudinal length of said emergence profile portion is greater in a lingual aspect than in a facial aspect, and an interproximal aspect of said shoulder slopes continuously apically from said lingual aspect to said facial aspect.

30. The dental abutment of claim 22 wherein said emergence profile portion further comprises at least a first convex surface having a radius of curvature and at least a first concave surface contiguous with said first convex surface.

31. The dental abutment of claim 30 further comprising a second convex surface having a second radius of curvature and adjacent said base portion, wherein said second radius of curvature is less than said first radius of curvature.

32. The dental abutment of claim 22 further comprising an internal longitudinal bore having a shoulder and a thread.

33. The dental abutment of claim 22 further comprising at least one flat portion in an upper interproximal region of said emergence profile portion.

34. The dental abutment of claim 22 wherein said tapered coronal portion comprises a center axis set at an angle from the abutment longitudinal axis.

35. A dental abutment having a longitudinal axis, the abutment comprising:
- a polygonal base portion for engagement with a dental implant;
- a tapered coronal portion having a non-frustoconical upper portion, and defining a coronal extremity spaced proximally from said base portion; the tapered coronal portion having an apical bottom;
- an emergence profile portion disposed between said base portion and said tapered coronal portion, said emergence profile portion generally defining a longitudinal direction and comprising:
  - at least a first concave surface,
  - at least a first convex surface contiguous with the first concave surface, and
  - a chamfer having an apical edge forming a junction with the base portion, and a coronal edge disposed apically relative to the first concave surface and the first convex surface such that the first concave surface and the first convex surface of the emergence profile portion are both disposed coronally relative to the coronal edge of the chamfer, wherein the chamfer forms a short ring so that the coronal edge is substantially closer to the apical edge than the first convex surface entirely around the abutment, and is sloped to extend radially outward as the chamfer extends coronally from the apical edge to the coronal edge,
  - wherein the combined longitudinal length of the first concave surface and the firs convex surface forms a longer portion of the emergence profile portion than the longitudinal length of the chamfer;
- an internal longitudinal bore having a shoulder and a threaded region,
- wherein said longitudinal length of said emergence profile portion is greater in a lingual aspect than in a facial aspect; and
- a margin shoulder positioned between the emergence portion and the apical bottom of the tapered coronal portion, the margin shoulder having a lingual side and a facial side, the margin shoulder extending interproximally from the lingual side to the facial side such that the margin shoulder continuously slopes apically from the apical bottom of the tapered coronal portion, wherein the facial side of the margin shoulder is positioned closer to the base portion than is the lingual side of the margin shoulder; the margin shoulder further defining an arcuate transition zone positioned axially along the apical bottom of the tapered coronal portion, the transition zone formed by an increasing radius of the apical bottom of the tapered coronal portion in an apical direction, such that the apical bottom of the tapered coronal portion flares continuously radially outwardly to the radially outermost edge of the margin shoulder,
- wherein the first concave surface and the first convex surface of the emergence profile portion are both disposed apically relative to the margin shoulder.

36. The dental abutment of claim 1 wherein the emergence profile further comprises a substantially cylindrical surface between the chamfer and the first concave surface.

37. The dental abutment of claim 1 wherein the chamfer has a longitudinal length shorter than the longitudinal lengths of both the first concave surface and the first convex surface.

38. The dental abutment of claim 1 wherein the chamfer is continuously sloped from the apical edge to the coronal edge.

39. The dental abutment of claim 1 wherein the coronal edge defines a plane perpendicular to the longitudinal axis.

40. The dental abutment of claim 1 wherein the concave surface has an apical end with a diameter of 3.5 millimeters, and wherein the convex surface has a coronal end with a diameter of 4.7 millimeters.

* * * * *

UNITED STATES PATENT AND TRADEMARK OFFICE
CERTIFICATE OF CORRECTION

PATENT NO. : 8,506,296 B2  
APPLICATION NO. : 11/380560  
DATED : August 13, 2013  
INVENTOR(S) : Bassett et al.

Page 1 of 1

It is certified that error appears in the above-identified patent and that said Letters Patent is hereby corrected as shown below:

On the Title Page, Item (56)

On page 2, in column 2, under "Other Publications", line 1-2, delete "International Search Report from PCT/US06/23128 Dated Sep. 24, 2007." and insert --"International Application Serial No. PCT/US2006/023128, International Search Report mailed Sep. 24, 2007."--, therefor On page 2, in column 2, under "Other Publications", line 3, before "Extended", insert --"--, therefor On page 2, in column 2, under "Other Publications", line 3, delete "supplementary" and insert --Supplementary--, therefor On page 2, in column 2, under "Other Publications", line 5, delete "dated" and insert --mailed--, therefor On page 2, in column 2, under "Other Publications", line 5, after "2009", insert --"--, therefor On page 2, in column 2, under "Other Publications", line 6, before "Extended", insert --"--, therefor On page 2, in column 2, under "Other Publications", line 6, delete "supplementary" and insert --Supplementary--, therefor On page 2, in column 2, under "Other Publications", line 8, delete "dated" and insert --mailed--, therefor On page 2, in column 2, under "Other Publications", line 8, after "2009", insert --"--, therefor In the Claims In column 27, line 29, in Claim 35, delete "firs" and insert --first--, therefor Signed and Sealed this  
Twenty-fourth Day of December, 2013

Margaret A. Focarino  
*Commissioner for Patents of the United States Patent and Trademark Office*